(12) United States Patent
Alajem et al.

(10) Patent No.: US 8,507,260 B2
(45) Date of Patent: Aug. 13, 2013

(54) MULTISTEP REACTION LATERAL FLOW CAPILLARY

(75) Inventors: Sara Alajem, Kfar-HaNagid (IL); Avraham Reinhartz, Gan-Yavne (IL)

(73) Assignee: Realbio Technologies, Ltd., Kfar-Hanigid (IL)

( * ) Notice: Subject to any disclaimer, the term of this patent is extended or adjusted under 35 U.S.C. 154(b) by 358 days.

(21) Appl. No.: 12/791,944

(22) Filed: Jun. 2, 2010

(65) Prior Publication Data

US 2010/0239459 A1   Sep. 23, 2010

Related U.S. Application Data

(62) Division of application No. 11/883,329, filed as application No. PCT/IL2006/000121 on Jan. 31, 2006.

(60) Provisional application No. 60/647,774, filed on Jan. 31, 2005.

(51) Int. Cl.
    *C12M 1/34* (2006.01)

(52) U.S. Cl.
    USPC ........ 435/287.7; 73/61.52; 73/61.54; 422/50; 422/68.1; 422/69; 422/70; 422/400; 422/408; 422/412; 422/420; 422/421; 422/423; 422/424; 422/425; 422/426; 422/428; 422/429; 435/287.1; 435/287.2; 435/287.3; 435/287.8; 435/287.9; 435/4; 435/7.1; 435/975; 436/161; 436/162

(58) Field of Classification Search
    USPC ................ 73/61.52, 61.54; 422/68.1, 69, 70, 422/50, 400–404, 408, 412, 420–430; 435/287.1–287.3, 287.7–287.9, 4–40; 436/161, 436/162
    See application file for complete search history.

(56) References Cited

U.S. PATENT DOCUMENTS

| | | | |
|---|---|---|---|
| 4,623,461 A | 11/1986 | Hossom et al. | |
| 4,632,901 A | 12/1986 | Valkirs et al. | |

(Continued)

FOREIGN PATENT DOCUMENTS

| | | |
|---|---|---|
| EP | 0284232 | 9/1988 |
| EP | 1236514 | 9/2002 |

(Continued)

OTHER PUBLICATIONS

Jallerat et al. "Filter Membranes and Bioseparation Equipment and Supplies", IVD Technology, Oct. 2002, 4 pages.

(Continued)

*Primary Examiner* — Melanie Y Brown
*Assistant Examiner* — Erik B Crawford
(74) *Attorney, Agent, or Firm* — Woodcock Washburn, LLP

(57) ABSTRACT

Disclosed is a lateral flow capillary device and uses thereof comprising a unipath bibulous capillary flow matrix and at least two reservoirs each in fluid communication with the capillary flow matrix wherein a reservoir contacts the capillary flow matrix through a passage having a rim pressing the matrix. The pressure that the rim applies on the matrix prevents leakage of liquids out of the capillary flow matrix at the reservoir/ matrix interface, allowing accurate sequential draining of liquid from the reservoirs. During use of the disclosed lateral flow capillary device a static interface is formed between the first liquid and the second liquid in an interface creation zone inside the capillary flow matrix wherein the first amount and second amount are such that first liquid substantially remains in the first reservoir and the second liquid substantially remains in the second reservoir subsequent to the formation of the static interface and wherein the interface begins to move only subsequent to exhaustion of a liquid from a reservoir.

4 Claims, 9 Drawing Sheets

(56) References Cited

U.S. PATENT DOCUMENTS

| | | | |
|---|---|---|---|
| 4,818,677 A * | 4/1989 | Hay-Kaufman et al. | ......... 435/4 |
| 4,855,240 A | 8/1989 | Rosenstein et al. | |
| 4,861,711 A | 8/1989 | Friesen et al. | |
| 4,960,691 A | 10/1990 | Gordon et al. | |
| 4,981,786 A | 1/1991 | Dafforn et al. | |
| 5,081,017 A | 1/1992 | Longoria | |
| 5,089,389 A | 2/1992 | Pelanek | |
| 5,120,643 A | 6/1992 | Ching et al. | |
| 5,198,193 A | 3/1993 | Bunce et al. | |
| 5,223,220 A | 6/1993 | Fan et al. | |
| 5,821,073 A | 10/1998 | Lee | |
| 5,853,670 A | 12/1998 | Bunce | |
| 6,297,020 B1 | 10/2001 | Brock | |
| 6,464,939 B1 | 10/2002 | Bachand et al. | |
| 6,634,243 B1 | 10/2003 | Wickstead et al. | |
| 6,812,038 B1 | 11/2004 | Mendel-Hartvig | |
| 2003/0171698 A1 | 9/2003 | Rubin et al. | |
| 2004/0015101 A1 | 1/2004 | Rubin et al. | |
| 2008/0145835 A1 | 6/2008 | Alajem et al. | |

FOREIGN PATENT DOCUMENTS

| | | |
|---|---|---|
| EP | 1044372 | 9/2003 |
| WO | WO 01/27626 | 4/2001 |
| WO | WO 02/06830 | 1/2002 |
| WO | WO 2005/031355 | 4/2005 |
| WO | WO 2006/087697 | 8/2006 |

OTHER PUBLICATIONS

Jones et al. "Effects of Adhesive Migration in Lateral Flow Assays", IVD Technology, Sep. 2000, 8 pages.

Millipore Corporation Product Literature, "Rapid Lateral Flow Test Strips", May 2008, 42 pages.

* cited by examiner

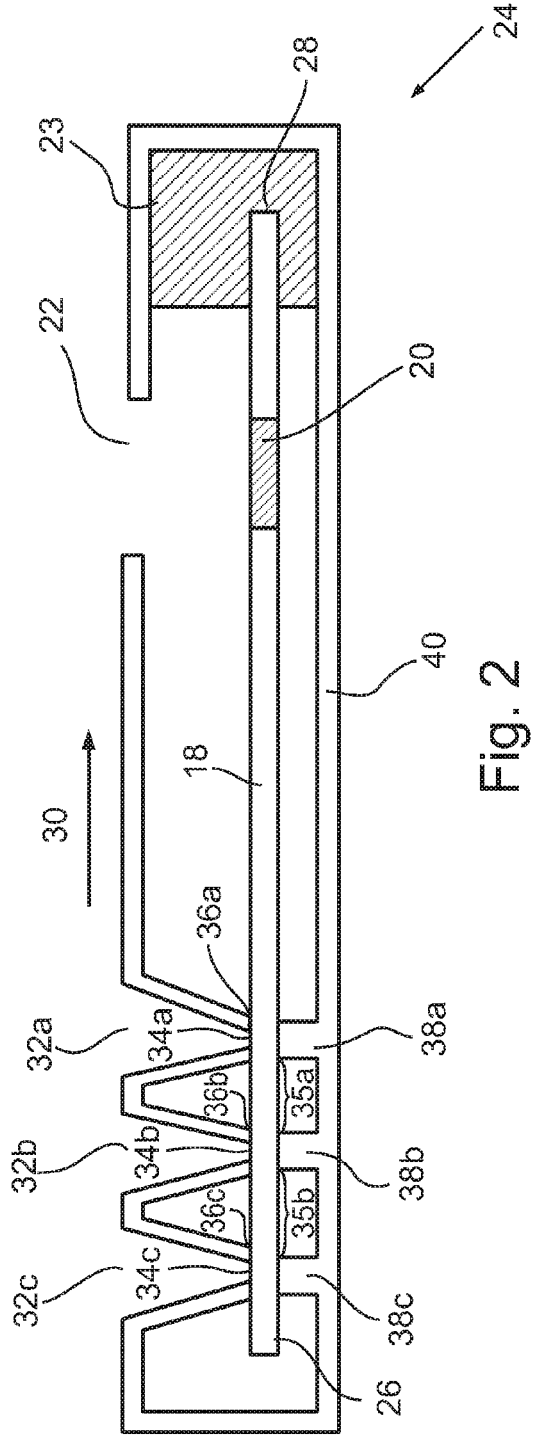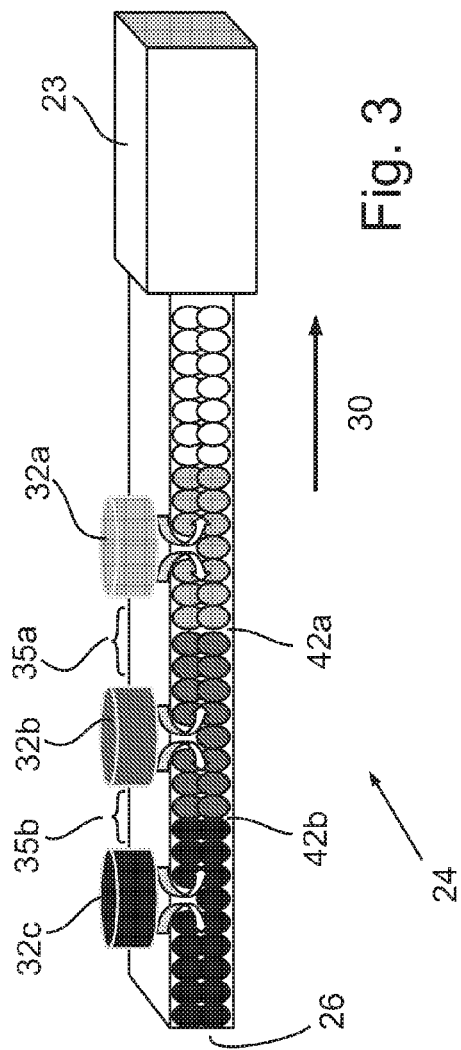

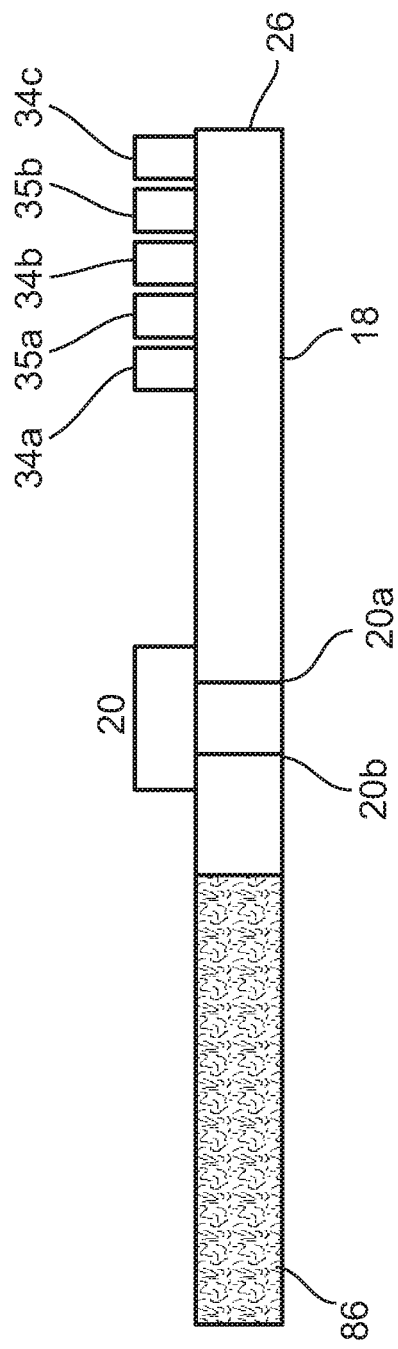
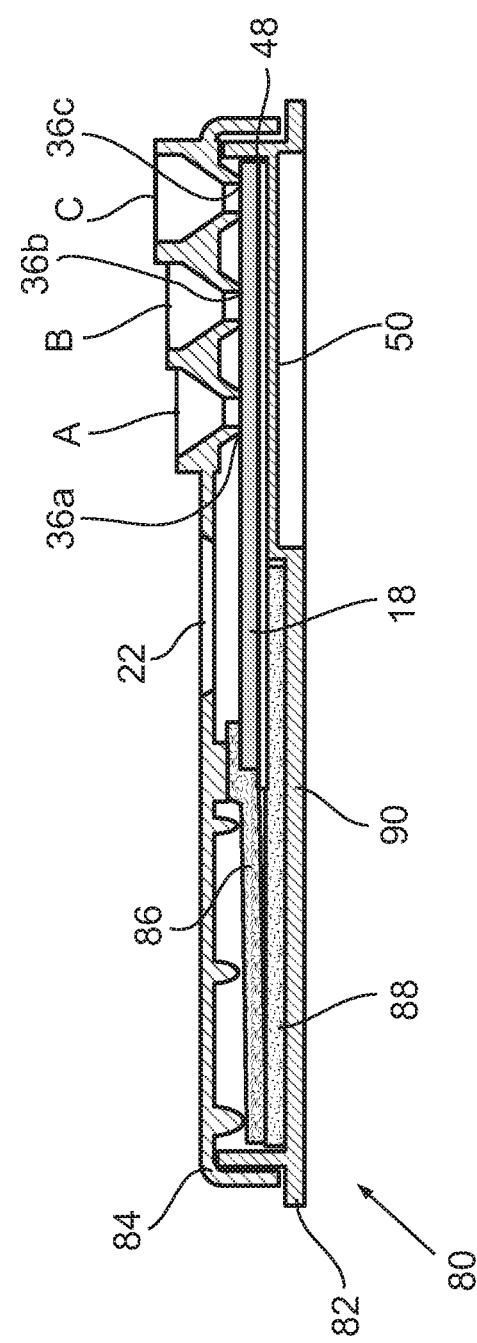

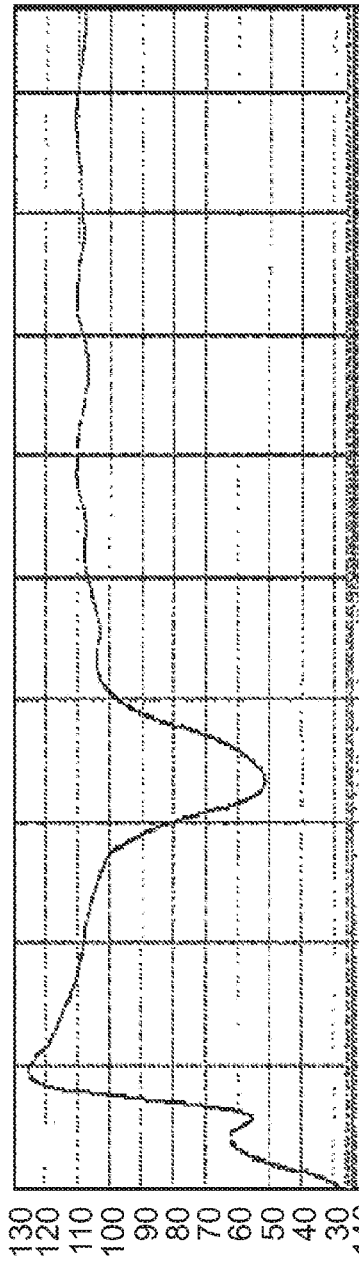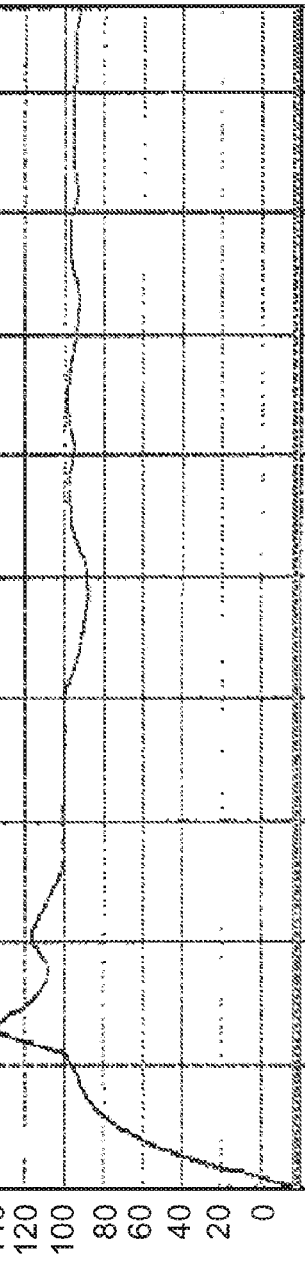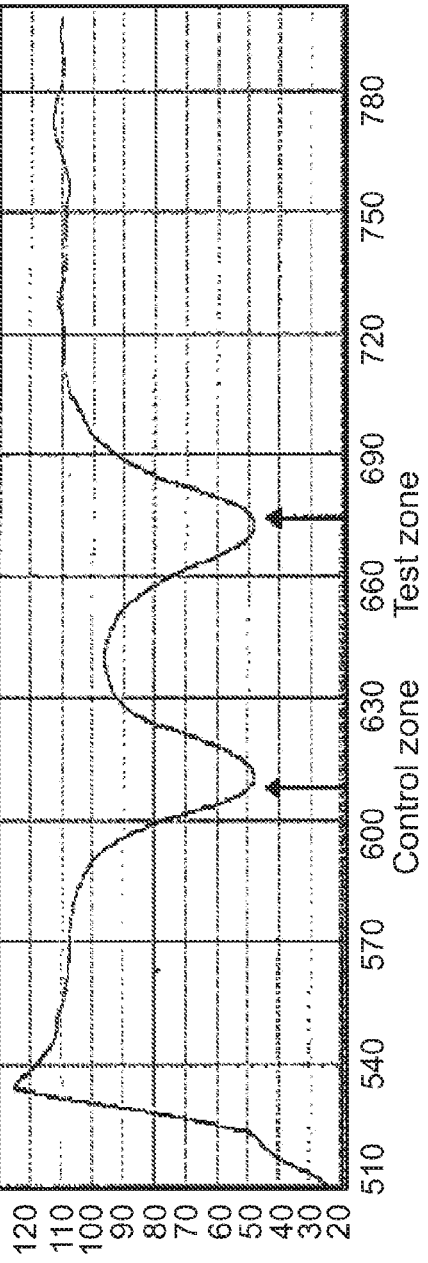

MULTISTEP REACTION LATERAL FLOW CAPILLARY

CROSS-REFERENCE TO RELATED APPLICATIONS

This application is a divisional of application Ser. No. 11/883,329, filed on Jul. 30, 2007, which is a National Phase of PCT Patent Application No. PCT/IL2006/000121 having International Filing Date of Jan. 31, 2006, which claims the benefit of U.S. Provisional Patent Application No. 60/647,774 filed on Jan. 31, 2005. The contents of the above Applications are all incorporated herein by reference.

FIELD AND BACKGROUND OF THE INVENTION

The present invention relates to the field of biology and detection of analytes from environmental and biological fluids, mainly at points-of-care more particularly, to an improved lateral flow capillary device and methods for using lateral flow capillary devices, for example for performing specific binding assays.

The use of specific binding assays is of great value in a variety of clinical and other applications, see for example PCT patent application US2004/031220 published as WO 2005/031355. Specific binding assays involve the detection and preferably quantitative determination of an analyte in a sample where the analyte is a member of a specific binding pair consisting of a ligand and a receptor. The ligand and the receptor constituting a specific binding pair are related in that the receptor and ligand specifically mutually bind. Specific binding assays include immunological assays involving reactions between antibodies and antigens, hybridization reactions of DNA and RNA, and other specific binding reactions such as those involving hormone and other biological receptors. Specific binding assays may be practiced according to a variety of methods known to the art. Such assays include competitive binding assays, "direct" and "indirect" sandwich assays as described, for example, in U.S. Pat. Nos. 4,861,711; 5,120,643; 4,855,240 or EP 284,232.

Because the complex formed by a specific binding reaction is generally not directly observable various techniques have been devised for labeling one member of the specific binding pair in order that the binding reaction may be observed. Known labels include radiolabels, chromophores and fluorophores and enzymes the presence of which may be detected by means of radiation detectors, spectrophotometers or the naked eye. When a member of a specific binding pair is tagged with an enzyme label, a complex may be detected by the enzymatic activation of a reaction system including a signal generating substrate/cofactor group wherein a compound such as a dyestuff, is activated to produce a detectable signal.

Lateral flow capillary devices, such as lateral flow capillary device 10 depicted in FIG. 1, are well known in the fields of analysis and detection and are often used for quick and simple implementation of specific binding assay of analyte in a liquid sample 12. Sample 12 is placed in lateral flow capillary device 10 through a reservoir 14 to contact a liquid receiving zone 16 of a bibulous capillary flow matrix 18. Receiving zone 16 includes a soluble labeled reagent configured to bind to the analyte which present in the sample 12. Sample 12 including the analyte bound to the labeled reagent, migrates by capillary flow to fill all of capillary flow matrix 18 and to migrate further into liquid drain 23. During the capillary flow of sample 12 from liquid receiving zone 16 towards liquid drain 23, sample 12 passes reaction zone 20 which is observable through an observation window 22. Reaction zone 20 comprises an anti-analyte that together with the analyte constitutes a specific binding pair. Analyte in sample 20 forms a complex with the anti analyte and is thus captured at reaction zone 20. As the labeled reagent is bound to the analyte, and as the analyte is concentrated at reaction zone 20, an observable signal is produced at the reaction zone 20, where the intensity of the observable signal is related to the amount of analyte in the sample.

Lateral flow capillary devices such as device 10 are extremely useful as these are simple to operate even by an unskilled person or under non-laboratory conditions and are relatively cheap to produce.

One drawback of known lateral flow capillary devices such as device 10 is that a sample evenly spreads in all directions until a border to capillary flow is encountered, such as an edge of the capillary flow matrix. Thus, sample and any analyte therein are distributed within the entire volume of the capillary flow matrix and wasted. It would be advantageous to be able to enable transport of all of a sample added to a capillary flow matrix to the vicinity of a respective reaction zone.

An additional drawback of known lateral flow capillary devices is that these are not configured for multistep reactions. To perform a multistep binding assay using a lateral flow capillary device such as device 10, reagent liquids are added serially. For example, a device 10 is provided where a liquid receiving zone 16 does not include a labeled reagent.

First, a sample 12 including analyte is added through reservoir 14, passes into capillary flow matrix 18 through liquid receiving zone 16 and is transported by capillary flow to drain 23. When sample 12 passes through reaction zone 20, analyte in sample 20 forms a complex with the anti analyte located at reaction zone and is thus captured at reaction zone 20.

When all of sample 12 has drained into capillary flow matrix 18, a first reagent liquid containing a labeled reagent configured to bind to the analyte is added through reservoir 14, passes into capillary flow matrix 18 through liquid receiving zone 16 and is transported by capillary flow to drain 23. When the first reagent liquid passes through reaction zone 20, labeled reagent in the first reagent liquid binds to analyte captured at the reaction zone.

When labeled reagent includes an enzyme, then when all of the first reagent liquid has drained into capillary flow matrix 18, a second reagent liquid containing an enzyme substrate is added through reservoir 14, passes into capillary flow matrix 18 through liquid receiving zone 16 and is transported by capillary flow to drain 23. When the second reagent liquid passes through reaction zone 20, the enzyme substrate therein reacts with the enzyme label, producing a strong observable signal at the reaction zone 20, where the intensity of the observable signal is related to the amount of analyte in the sample.

It is known that multistep binding assays are significantly more sensitive and accurate than single step binding assays. Thus, there is a desire to perform multi step binding assays as described above. It is clear, however, that it is very difficult if not impossible to achieve accurate and repeatable results for such a complex process without the use of an expensive robotic system located in a laboratory. Even with the use of a robotic system, since any succeeding liquid is added onto a liquid receiving zone 16 already wet with a preceding liquid, mixing of the two liquids invariably occurs, leading to unpredictable result, adversely affecting duration of any given step, preventing performance of a truly sequential reaction, and affecting repeatability and accuracy.

In U.S. Pat. No. 5,198,193 is taught a flow capillary device with multiple capillary paths leading towards a single reaction zone, each path having a different length and/or a valve to allow variation of timing of arrival of a liquid to the reaction zone. Such a device is ineffective as at each intersection of capillary paths including two different liquids, parallel flows are produced, analogous to the produced when a succeeding liquid is added onto an already wet capillary flow matrix as discussed above. Further, the valves described in such a lateral flow capillary device are difficult to fabricate.

In European Patent No. EP 1044372 is taught a lateral flow capillary device where sample and reagent liquids are added at two or more adjacent positions along a capillary flow matrix that is substantially a strip of bibulous material, e.g., 8 micron pore size polyester backed nitrocellulose. N+1 narrow (e.g., 1 mm) spacers, impermeable hydrophobic strips of material (mylar or polyester sticky tape) are placed perpendicularly to the flow direction to define N broad (e.g., 5 mm) liquid receiving zones upstream of a reaction zone located upstream of a liquid drain. When liquids are added simultaneously to the liquid receiving zones a portion of each liquid is absorbed through the upper surface of the capillary flow matrix at the liquid receiving zone. Liquid that is not immediately absorbed remains as drops on the surface of a respective liquid receiving zone, where adjacent drops are prevented from mixing or flowing along the surface of the capillary flow matrix by the spacers. In cases where the liquids are added simultaneously an interface between the two liquids is formed in the volume of the matrix underneath the spacer, while excess liquid remains on the surface of a liquid receiving zone. Liquid from a first, most downstream, liquid receiving zone is transported downstream by capillary flow past the reaction zone to the liquid drain. When all the liquid in the first liquid receiving zone is exhausted, the second liquid receiving zone is transported downstream by capillary flow past the reaction zone to the liquid drain.

Seemingly the teachings of EP 1044372 provide the ability to perform multistep reactions using a lateral flow capillary device, but practically the teachings are severely limited by limitations imposed by the structure of the lateral flow capillary device.

A first limitation is that the amount of liquid added to a liquid receiving zone is limited. The liquid is added as a drop resting on a liquid receiving zone. If the surface tension of the liquid is unsufficient, for example due to size or due to detergents in the liquid, if the capillary flow matrix is highly hydrophillic or if the lateral flow capillary device is perturbed, the drop collapses and spills from the lateral flow capillary device.

A second limitation is that the liquids must be added simultaneously. If liquids are added non-simultaneously, a liquid added to a first liquid receiving zone flows into a second, adjacent, liquid receiving zone. When a second liquid is added to the second liquid receiving zone, the second liquid flows into a volume of the matrix from the top through dry parts of the second liquid receiving zone while the second liquid flows into the same volume laterally. The two liquids mix, and as discussed above, leads to unpredictable result, adversely affects duration of a given step, prevents performance of a truly sequential reaction, and affects both repeatability and accuracy of the results.

A third limitation is that the teachings of EP 1044372 may lead to the formation of multiple capillary paths. As noted above, a spacer is a strip of smooth material attached using adhesive to the top surface of the matrix that has micron scale features. As a result, capillary paths are formed in the space between a spacer and the capillary flow matrix through which two liquids in adjacent liquid receiving zones may be mixed and as discussed above, leads to unpredictable result, adversely affects duration of a given step, prevents performance of a truly sequential reaction, and affects both repeatability and accuracy of the results.

An additional disadvantage of the teachings of EP 1044372 is the reliance on adhesives for securing the spacers to the capillary flow matrix. In the art it is known that adhesives, especially non-polymerizing adhesives, are attracted by and over time migrate into bibulous materials such as nitrocellulose that are suitable for use as capillary flow matrices (see, for example, Kevin Jones; Anne Hopkins, Effect of adhesive migration in lateral flow assays; IVD Technology, September 2000). Thus, after a period of storage, the adhesive securing a spacer to a capillary flow matrix of a device made in accordance with the teachings of EP 1044372 would migrate into the pores of the capillary flow matrix in the region where the liquid-liquid interface is to form. The presence of a hydrophobic adhesive in the matrix blocks pores or modify the capillary properties of the pores so that an interface formed between liquids is indefinite and not clear, leading to mixing of the two liquids of the interface and concomitant negative effects. Another disadvantage of using adhesives is the possible detachment of the spacers from the matrix during prolonged storage.

In U.S. Pat. No. 4,981,786 is taught a lateral flow capillary device with two reservoirs. The provision of a lateral flow capillary device with two or more reservoirs allows addition of two or more succeeding liquids without mutual contamination: once a liquid has been added to a first reservoir, remnants of the liquid remain on the walls of the reservoir. Any liquid added through the same reservoir will be contaminated with the remnants. In a first lateral flow capillary device taught in U.S. Pat. No. 4,981,786, two or three distinct reservoirs are in fluid communication with a capillary flow matrix through distinct and physically separated liquid receiving zones. Located at one of the liquid receiving zones is a reaction zone including a trapping reagent. A liquid drain is in capillary communication with capillary flow matrix downstream from the two reservoirs. Although not entirely clear from the description, it is understood that the use of the first lateral flow capillary device includes adding a small volume of sample through a reservoir to provide a spot of sample at the reaction zone on the capillary flow matrix and subsequently to add one or more reagents, each reagent through a different reservoir.

In a second lateral flow capillary device taught in U.S. Pat. No. 4,981,786, two distinct reservoirs are in fluid communication with a capillary flow matrix through distinct and physically separated liquid receiving zones. In capillary communication with the upstream edge of the capillary flow matrix is a liquid reservoir that may be activated to release a reagent liquid that subsequently migrates downstream. A reaction zone is located downstream from the two reservoirs. A liquid drain is in capillary communication with capillary flow matrix downstream from the reaction zone.

In both lateral flow capillary devices are taught a number of structural features to keep a capillary flow matrix in place but make only minimal contact therewith. Further, it is noted that there is little or no contact between a reservoirs and the capillary flow matrix at a respective liquid receiving zone, and if there is contact it is only light contact resulting from swelling of the capillary flow matrix upon wetting. Such features preclude the use of the lateral flow capillary devices as effective devices for multistep reactions in a manner analogous to the disclosed in EP 1044372. When a first liquid is added to a first reservoir and simultaneously a second liquid is added to a second adjacent upstream reservoir, the first and second liquids both flow into the capillary flow matrix through a respective liquid receiving zone. When the two liquids meet, an interface is formed and the first liquid begins to flow downstream. Uncontrollably, liquid begins to leak from the capillary flow matrix at any point where an alternate capillary path exists, for example down the supporting structures on which the capillary flow matrix rests or along the laterally disposed walls that hold the capillary flow matrix in place. Liquid also climbs up any object contacting the upper surface of the capillary flow matrix, for example where a reservoir contacts the capillary flow matrix. As a result, liquid leaks away from all liquid receiving zones through any alternative capillary path, filling the lateral flow capillary device with liquid and rendering results of an experiment useless.

It would be highly advantageous to have a lateral flow capillary device or methods for using lateral flow capillary devices for the performance of multistep reactions in the fields of biology and medicine, particularly for diagnosis not having at least some of the disadvantages of the prior art.

SUMMARY OF THE INVENTION

Embodiments of the present invention successfully address at least some of the shortcomings of the prior art by providing a lateral flow capillary device and a method including the use of a lateral flow capillary device allowing performance of multistep reactions. Embodiments of the present invention allow performance of multistep reactions such as multistep binding assays accurately and repeatably even in non-laboratory conditions and even by less skilled operators.

According to the teachings of the present invention there is provided a lateral flow capillary device comprising: a) a unipath bibulous capillary flow matrix having an upstream end and a downstream end defining a flow direction; b) at least two reservoirs in fluid communication with the capillary flow matrix each through at least one respective liquid receiving zone; wherein a reservoir contacts a respective liquid receiving zone through an opening constituting a hollow conduit having a rim pressing the matrix and wherein a portion of the capillary flow matrix between the two rims is an interface creation zone.

In embodiments of the present invention, the pressing is such that liquid-induced swelling of the matrix is constrained, that is when the matrix is wet and swells, the rims apply pressure resisting the swelling.

In embodiments of the present invention, the rims press the matrix when the matrix is dry. In embodiments of the present invention the rims are pressed into the matrix when the matrix is dry.

In embodiments of the present invention, the rims are substantially parallel to the flow direction.

In embodiments of the present invention, pressure applied by a rim is substantially uniform about the entire surface of the rim.

In embodiments of the present invention, the matrix is substantially compressible, that is does not break under pressure which leads to a reduction in volume of the matrix yet substantially retains structural integrity. In embodiments of the present invention, the internal surface-area volume$^{-1}$ of the matrix proximate to a rim is higher than distant from the rim.

In embodiments of the present invention, the matrix comprises or even essentially consists of glass fibers and/or nitrocellulose and/or porous polyethylene.

In embodiments of the present invention, opposite each rim is disposed a supporting component supporting the matrix against the pressing.

In embodiments of the present invention, the matrix is suspended between the rims and the supporting components.

In embodiments of the present invention the matrix is attached to a substantially impermeable backing. In embodiments of the present invention, the impermeable backing contacts at least one supporting component supporting the impermeable backing against the pressing. In embodiments of the present invention, opposite each rim is disposed a supporting component supporting the matrix against the pressing. In embodiments of the present invention, the matrix is suspended between the rims and the supporting components.

In embodiments of the present invention, the lateral flow capillary device further comprises downstream from at least one liquid receiving zone, a reaction zone comprising at least one capturing entity (e.g., a member of a specific binding pair) configured to capture a material (e.g., an analyte or a product of a reaction involving the analyte) flowing through the capillary flow matrix. In embodiments, the reaction zone is in a liquid receiving zone of a reservoir.

In embodiments of the present invention, the lateral flow capillary device further comprises downstream from at least two liquid receiving zones, a reaction zone comprising at least one capturing entity configured to capture a material flowing through the capillary flow matrix.

In embodiments of the present invention, the lateral flow capillary device further comprises a liquid drain in fluid communication with the capillary flow matrix downstream from at least two of the at least two reservoirs.

In embodiments of the present invention, the fluid communication through the liquid receiving zones is non-capillary communication.

In embodiments of the present invention, the interface creation zone is a volume of matrix with a length in the flow direction, and of a width and height substantially of the capillary flow matrix, that is the interface creation zone corresponds to a cross section of the matrix with a finite length. In embodiments of the present invention, the interface creation zone has a length of at least about 50%, at least about 75%, at least about 100%, even at least about 150%, and even at least about 400% of a dimension of a liquid receiving zone in the flow direction.

In embodiments of the device of the present invention, liquid induced swelling of the interface creation zone is unconstrained.

In embodiments of the present invention, a reservoir is substantially a container.

In embodiments of the present invention, the device further comprises a housing containing the capillary flow matrix. In embodiments of the present invention, sides of the capillary flow matrix are substantially devoid of contact with the housing.

According to the teachings of the present invention there is also provided a device useful for preparation of lateral flow capillary device, comprising: a) a first component, including a reservoir with at least one wall configured to hold liquids and a lowest area, the lowest area defined by a non-capillary opening defining a hollow conduit with a rim and at least one extension protruding from an outer surface of the wall; and b) a second component, including a body with a counter-support platform at a top-end and at least one extension protruding from the body wherein an extension of the first component and a extension of the second component are configured to mutually engage so that the rim and the counter-support platform are spaced apart and substantially parallel.

In embodiments of the present invention, the opening is a non-capillary opening, that is of dimensions that are not conducive to capillary flow therethrough.

In embodiments of the present invention, the opening has a cross-sectional area of at least about 1 mm$^2$, of at least about 3 mm$^2$ or even a cross-sectional area of at least about 7 mm$^2$.

In embodiments of the present invention, the first component and the second component each comprise at least two extensions.

In embodiments of the present invention, at least one first component extension and at least one second component extension together define a hinge when engaged.

In embodiments of the present invention, the mutual engaging includes interlocking, for example, by snapping together.

According to the teachings, of the present invention there is also provided a kit for assembly of a lateral flow capillary device, comprising: a) a unipath bibulous capillary flow matrix having a thickness; and b) at least two devices as described above, wherein the distance is sufficient so that a rim contacts the matrix when the two components are engaged about the matrix. In embodiments of the present invention, the distance is sufficient to clamp the matrix so as to press the rim into the matrix perpendicularly to the thickness when the two components are engaged. In embodiments of the present invention, the matrix is substantially a strip of material, for example comprising glass fiber.

In embodiments of the present invention, the matrix is attached to a substantially impermeable backing. In embodiments of the present invention, the backing is substantially planar. In embodiments of the present invention, the matrix together with the backing are substantially a strip.

In embodiments of the present invention, the capillary flow matrix includes a reaction zone comprising at least one capturing entity (e.g., a member of a specific binding pair) configured to capture a material (e.g., an analyte or a product of a reaction involving the analyte) flowing through the capillary flow matrix.

According to the teachings of the present invention there is also provided a method of performing a reaction comprising: a) providing a lateral flow capillary device as described above; b) adding a first amount of a first liquid to a first reservoir so that the first liquid flows into the capillary flow matrix through the respective liquid receiving zone; and c) adding a second amount of a second liquid to a second reservoir so that a second liquid flows into the capillary flow matrix through a respective liquid receiving zone; so that a static liquid-liquid interface is formed between the first liquid and a liquid in an interface creation zone; wherein the first amount and the second amount are such that first liquid substantially remains in the first reservoir and second liquid substantially remains in the second reservoir subsequent to formation of the static interface; and wherein the interface begins to move only subsequent to exhaustion of a liquid from a reservoir. Generally, the interface moves downstream upon exhaustion of the more downstream reservoir.

Generally, the static liquid-liquid interface is formed between the first liquid and the second liquid in the interface creation zone between the respective reservoirs to which the two liquids were added.

In embodiments, the static liquid-liquid interface is formed between the first liquid and a liquid in the matrix that is located between the liquid receiving zone associated with the first reservoir and the liquid receiving zone associated with the second reservoir. Such a situation occurs, for example when using a device provided with three reservoirs and three respective liquid receiving zones where in the reservoir associated with the most downstream liquid receiving zone is added an amount of the first liquid and in the reservoir associated with the most upstream liquid receiving zone is added an amount of the second liquid so that in neither case does all the liquid enter the matrix, but in the reservoir of the middle receiving zone is added an amount of a third liquid that entirely enters the matrix. In such a case two interfaces are formed: one between the first liquid and the third liquid and one between the third liquid and the second liquid.

In embodiments of the present invention, the first liquid and the second liquid are substantially identical, e.g., both are analyte containing sample. In embodiments of the present invention, the first liquid and the second liquid are substantially different, for example one is an analyte containing sample and one is a reagent liquid (e.g., a solution including signal producing label).

In embodiments of the present invention, the first amount and the second amount are substantially different. In embodiments of the present invention, the first amount and the second amount are substantially equal.

In embodiments of the present invention, adding of the second amount is subsequent to the adding of the first amount. In embodiments of the present invention, adding of the first amount and of the second amount is substantially simultaneous.

According to the teachings of the present invention there is also provided a method of performing a reaction comprising: a) providing a lateral flow capillary device as described above including: i) on the capillary flow matrix, a first liquid receiving zone in fluid communication with a first reservoir; ii) on the capillary flow matrix upstream of the first liquid receiving zone, a second liquid receiving zone in fluid communication with a second reservoir; iii) a first reagent disposed at a location inside the first reservoir and/or in the capillary flow matrix in proximity to the first liquid receiving zone or downstream therefrom; iv) a second reagent disposed at a location inside the second reservoir and/or in the capillary flow matrix in proximity to the second liquid receiving zone; b) adding a first amount of a first liquid to the first reservoir so that the first liquid flows into the capillary flow matrix through the first liquid receiving zone to contact the first reagent; c) adding a second amount of a second liquid to the second reservoir so that the second liquid flows into the capillary flow matrix through the second liquid receiving zone to contact the second reagent; so that a static interface is formed between the first liquid and the second liquid in the interface creation zone; wherein the first amount and the second amount are such that liquid substantially remains in the first reservoir and in the second reservoir subsequent to formation of the static interface; and wherein the interface begins to move only subsequent to exhaustion of the liquid from a reservoir.

In embodiments of the present invention, the first liquid and the second liquid are substantially identical, e.g., both are analyte containing sample. In embodiments of the present invention, the first liquid and the second liquid are substantially different, for example one is an analyte containing sample and one is a reagent liquid (e.g., a solution including signal producing label).

In embodiments of the present invention, the first amount and the second amount are substantially different. In embodiments of the present invention, the first amount and the second amount are substantially equal.

In embodiments of the present invention, downstream of the first liquid receiving zone on the capillary flow matrix is a reaction zone comprising at least one capturing entity configured to capture a material flowing through the capillary flow matrix.

In embodiments of the present invention, adding of the second amount and the adding of the first amount is sequential. In embodiments of the present invention, adding of the first amount and of the second amount is substantially simultaneous.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention.

In the drawings:

FIG. 2 schematically depicts an embodiment of a lateral flow capillary device of the present invention including three liquid reservoirs and a capillary flow matrix without a backing, in cross section;

FIG. 3 schematically depicts the formation of standing columns of liquid in a lateral flow capillary device in accordance with the method of the present invention;

FIG. 7 are results of experiment 2, described below, detection of an analyte in accordance with the teachings of the present invention;

PREFERRED EMBODIMENTS OF THE INVENTION

Figure 1:
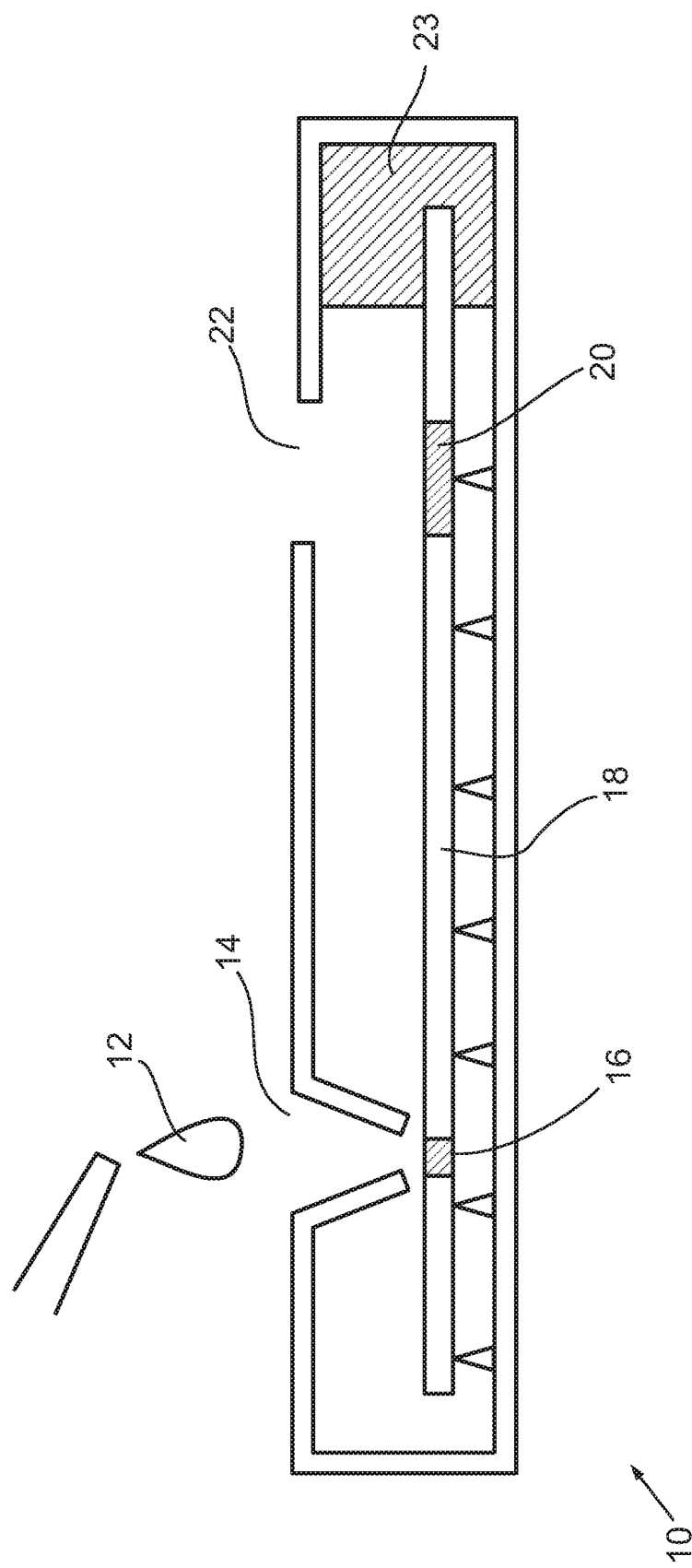
FIG. 1 (prior art) depicts a one reservoir lateral flow capillary device.

The present invention is of a lateral flow capillary device and methods of using the lateral flow capillary device. The present invention allows performance of effective and repeatable multistep reactions such as multistep specific binding assays for example for serological testing.

In the description the embodiments are directed to an analytical method for detecting an analyte that is a biomarker such as an antigen, antibody, metabolite, toxicant or other detectable material from human or other living source such as blood, urine, tissue, or from a non-living source such as an environmental source like water, soil or sewage. In the description the embodiments are directed to binding the analyte to an anti-analyte immobilized at a reaction zone on the capillary flow matrix which together with the analyte constitutes a specific binding pair such as an antibody, antigen, DNA or other specific binding pair (sbp) member and that the bound analyte is then detected directly or by a labeled reagent producing a detectable signal or that produces a detectable signal after being exposed to a third reagent which reacts with the labeled reagent and produces a detectable signal that can be visualized or measured by reading instrument.

The principles, uses and implementations of the teachings of the present invention may be better understood with reference to the accompanying description, figures and examples, perusal of which allows one skilled in the art to implement the teachings of the present invention without undue effort or experimentation. In the figures, like reference numerals refer to like parts throughout.

Before explaining at least one embodiment of the invention in detail, it is to be understood that the invention is not limited in its application to the details set forth herein. The invention can be implemented with other embodiments and can be practiced or carried out in various ways. It is also understood that the phraseology and terminology employed herein is for descriptive purpose and should not be regarded as limiting.

Generally, the nomenclature used herein and the laboratory procedures utilized in the present invention include techniques from the fields of biology, diagnostics engineering, material science and physics. Such techniques are thoroughly explained in the literature.

Unless otherwise defined, all technical and scientific terms used herein have the same meaning as commonly understood by one of ordinary skill in the art to which the invention belongs. In addition, the descriptions, materials, methods and examples are illustrative only and not intended to be limiting. Methods and materials similar or equivalent to those described herein can be used in the practice or testing of the present invention.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The term "method" refers to manners, means, techniques and procedures for accomplishing a given task including, but not limited to, those manners, means, techniques and procedures either known to, or readily developed from known manners, means, techniques and procedures by practitioners of the relevant arts. Implementation of the methods of the present invention involves performing or completing selected tasks or steps manually, automatically, or a combination thereof.

Herein, the term "analyte" refers to the compound or composition to be detected or quantitatively analyzed and which has at least one epitope or binding site. An analyte can be any substance for which there exist a naturally occurring analyte specific binding member or for which an analyte-specific binding member can be prepared. e.g., carbohydrate and lectin, hormone and receptor, complementary nucleic acids, and the like. Further, possible analytes include virtually any compound, composition, aggregation, or other substance which may be immunological detected. That is, the analyte, or portion thereof, will be antigenic or haptenic having at least one determinant site, or will be a member of a naturally occurring binding pair.

Analytes include, but are not limited to, toxins, organic compounds, proteins, peptides, microorganisms, bacteria, viruses, amino acids, nucleic acids, carbohydrates, hormones, steroids, vitamins, drugs (including those administered for therapeutic purposes as well as those administered for illicit purposes), pollutants, pesticides, and metabolites of or antibodies to any of the above substances.

Generally an analyte is found in a "sample" and the teachings of the present invention are applied to the sample to determine the presence of or an amount of analyte present in a sample.

Herein the term "sample" refers to anything which may contain an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). In addition, a solid material suspected of containing the analyte can be used as the test sample once it is modified to form a liquid medium or to release the—analyte. Pretreatment may involve preparing plasma from blood, diluting viscous fluids, and the like. Methods of treatment can involve filtration, distillation, separation, concentration, inactivation of interfering components, and the addition of reagents. Besides physiological fluids, other samples can be used such as water, food products, soil extracts, and the like for the performance of industrial, environmental, or food production assays as well as diagnostic assays. The selection and pretreatment of biological, industrial, and environmental samples prior to testing is well known in the art and need not be described further.

As used herein, the term "specifically binds" refers to the binding specificity of a "Specific binding pair member" which is a member of a specific binding pair, i.e., two different molecules wherein one of the molecules specifically binds with the second molecule through chemical or physical means. The two molecules are related in the sense that their binding with each other is such that they are capable of distinguishing their binding partner from other assay constituents having similar characteristics. The members of the specific binding pair are referred to as ligand and receptor (anti ligand), sbp member and sbp partner, and the like. A molecule may also be a sbp member for an aggregation of molecules; for example an antibody raised against an immune complex of a second antibody and its corresponding antigen may be considered to be an sbp member for the immune complex.

In addition to antigen and antibody specific binding pair members, other specific binding pairs include, as examples without limitation, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), metals and their chelators, and the like. Furthermore, specific binding pairs can include members that are analogs of the original specific binding member, for example an analyte-analog or a specific binding member made by recombinant techniques or molecular engineering.

A sbp member is analogous to another sbp member if they are both capable of binding to another identical complementary sbp member. Such a sbp member may, for example, be either a ligand or a receptor that has been modified by the replacement of at least one hydrogen atom by a group to provide, for example, a labeled ligand or labeled receptor. The sbp members can be analogous to or complementary to the analyte or to an sbp member that is complementary to the analyte. If the specific binding member is an immunoreactant it can be, for example, an antibody, antigen, hapten, or complex thereof. If an antibody is used, it can be a monoclonal or polyclonal antibody, a recombinant protein or antibody, a chimeric antibody, a mixture(s) or fragment (s) thereof, as well as a mixture of an antibody and other specific binding members. The details of the preparation of such antibodies and their suitability for use as specific binding members are known to those skilled in the art.

"Labeled reagent" refers to a substance comprising a detectable label attached with a specific binding member. The attachment may be covalent or non-covalent binding, but the method of attachment is not critical to the present invention. The label allows the label reagent to produce a detectable signal that is related to the presence of analyte in the sample. The specific binding member component of the label reagent is selected to directly bind to the analyte or to indirectly bind the analyte by means of an ancillary specific binding member, which is described in greater detail hereinafter.

In addition, the specific binding member may be labeled before or during, the performance of the assay by means of a suitable attachment method.

"Label" refers to any substance which is capable of producing a signal that is detectable by visual or instrumental means. Various labels suitable for use in the present invention include labels which produce signals through either chemical or physical means. Such labels can include enzymes, fluorescent compounds, chemiluminescent compounds, and radioactive labels. Other suitable labels include particulate labels such as colloidal metallic particles such as gold, colloidal non-metallic particles such as selenium, dyed or colored particles such as a dyed plastic or a stained microorganism, organic polymer latex particles and liposomes, colored beads, polymer microcapsules, sacs, erythrocytes, erythrocyte ghosts, or other vesicles containing directly visible substances, and the like. Typically, a visually detectable label is used as the label component of the label reagent, thereby providing for the direct visual or instrumental readout of the presence or amount of the analyte in the test sample without the need for additional signal producing, components at the detection sites.

The selection of a particular label is not critical to the present invention, but the label will be capable of generating a detectable signal either by itself, or be instrumentally detectable, or be detectable in conjunction with one or more additional signal producing components.

A variety of different label reagents can be formed by varying either the label or the specific binding member component of the label reagent; it will be appreciated by one skilled in the art that the choice involves consideration of the analyte to be detected and the desired means of detection. As discussed below, a label may also be incorporated used in a control system for the assay.

For example, one or more signal producing components can be reacted with the label to generate a detectable signal. If the label is an enzyme, then amplification of the detectable signal is obtained by reacting the enzyme with one or more substrates or additional enzymes and substrates to produce a detectable reaction product.

Labeled enzymes used in the field include, for example, Alkaline phosphatase, Horseradish peroxidase, Glucose oxidase and Urease.

In an alternative signal producing system, the label can be a fluorescent compound where no enzymatic manipulation of the label is required to produce the detectable signal. Fluorescent molecules include, for example, fluorescein, phycobiliprotein, rhodamine and their derivatives and analogs are suitable for use as labels in such a system.

The use of dyes for staining biological materials, such as proteins, carbohydrates, nucleic acids, and whole organisms is documented in the literature. It is known that certain dyes stain particular materials preferentially based on compatible chemistries of dye and ligand. For example, Coomassie Blue and Methylene Blue for proteins, periodic acid-Schiffs reagent for carbohydrates, Crystal Violet, SafraninO, and Trypan Blue for whole cell stains, Ethidium bromide and Acridine Orange "Signal producing component" refers to any substance capable of reacting directly or indirectly with the labeled reagent to produce signal that is detectable by visual or instrumental means. The component may be substrate catalyzed by the labeled enzyme or dyes that may react chemically with the label reagent (dsDNA/Acridine Orange), enzymes substrate such as: BCIP/NBT; Azonaphtol phosphate; 3-AEC; 4-chloronaphthol; tetrazolium salt/PMS; Urea/PH indicators.

In embodiments of the present invention, a capillary flow matrix includes at least one reaction zone. A reaction zone is a region or volume of the matrix comprising at least one capturing entity configured to capture a material flowing through the capillary flow matrix in defined regions for conducting the assay reaction including a test line and a control line. A "test line" is the region in the reaction zone, in which the analytical assay is performed. The region comprises specific binding pair (sbp) member which is immobilized to the matrix of the capillary path. The sbp member can be an antibody or antigen nucleic acid or modifications of the above. It may by proteins like avidin and its derivatives or saccharides such has lectins. Which are part of binding pair being capable of binding directly or indirectly the analyte of interest. Several test line may be in the reaction zone each of a distinct specific binding pair for different analytes. A "control line" is the region in the reaction zone, in which a reaction for confirming the validity of the assay is performed; the control line may also be a calibration line or lines for correction of the assay signals (results) obtained in the test line. The control line comprise of immobilized spb member with binding abilities to one or more of the reagents participating in the reaction or compounds existing in the sample.

In the present invention, a capillary flow matrix is bibulous, that is comprises a bibulous, porous or other cavity shaped material allowing capillary transport of liquids therethrough, that is the pores define a continuous system of capillary flow channels. Generally, for aqueous liquids capillary transport requires a continuous path of pores of less than about 2 mm in size, generally in the range of 0.05 microns to 100 microns. As is described herein, a suitable capillary flow matrix is substantially compressible, that is to say, retains structural integrity and does not break under applied pressure which leads to a reduction in volume, for example pressure applied by the reservoir rims. In embodiments, pressure applied to a capillary flow matrix perpendicularly by a reservoir rim compresses the capillary flow matrix to substantially same extent through the entire height of the capillary flow matrix. In embodiments, a matrix is thick enough and soft enough so that compression caused by applied pressure is local to the pressing. In embodiments, pressure applied by a rim to a capillary flow matrix substantially compresses the matrix and reduces the internal surface-area volume$^{-1}$ to a depth of no more than 40% of the thickness.

"Bibulous material" include but are not limited to materials composed of glass fiber paper or derivatized glass fiber paper, cellulose and its derivatives, nylons, PVDF, polysulfones, PTFE and polypropylene, paper and derivatized paper, see Eric Jallerat and Volkmar Thom, "Filter membranes and bioseparation equipment and supplies" by IVD Technology (2004) or catalogues of manufacturers such as Millipor Corp. (Bedford, Mass., USA), Watman Inc. (New Jersey, USA) or Ahlstrom Corp. (Helsinki, Finland).

Typically, the bibulous member consists of a series of fibers drawn together in parallel to form an open wick with some mechanical integrity due to bonding between the fibers, with the space between the fibers acting to form channels, which draw up liquid. Suitable fibers include polyester, polyamides such as nylons, and bicomponent fibers such as polyethylene/polyester, nylon/polyester and the like. Bicomponent polyethylene/polyester fibers typically comprise a polyester central core with an external sheath of polyethylene Inherently hydrophobic fibers such as polypropylenes can also be used provided they are water wettable or, if necessary, are rendered water wettable by other components such as surfactants or hydrophilic polymers. In principle any wettable fiber is suitable.

Fibers can be formed into a bibulous member by a variety of processes, such as annealing to partially melt the surface/sheath region and cause interpenetration of the polymer chains, which set on cooling see. Alternatively, adhesives, such as latex adhesives, may be used.

Capillary matrices of embodiments of the invention are of various forms including but not limited to sheets, columns, membranes, and compressed fibers. Suitable materials include but are not limited to porous materials and fibrous materials, including woven, rationally oriented and randomly oriented fibrous materials. Suitable materials include polymeric materials such as porous polymers including porous polyethylene, polypropylene, polytetrafluoroethylene (PTFE), ethylene vinyl acetate (EVA), polyether sulfone (PS), thermoplastic urethane (TPU), polyamide (e.g., Nylon 6) and copolymers thereof such as porous polymers manufactured by the Porex Corporation, Fairburn Ga., USA. Suitable materials include fibrous materials such as cellulose, cellulosic materials, cellulose derivatives, glass fibers, paper, filter paper, chromatographic paper, synthetic or modified naturally occurring polymers, such as nitrocellulose, cellulose acetate and cotton.

In embodiments, a bibulous capillary flow matrix of the present invention is a uniform structure such as strip of paper or a combination of several materials comprising a unipath structure. In embodiments a capillary flow matrix of the present invention is attached to a substantially impermeable backing material, for example as is known in the field of thin-layer chromatography where porous fibrous matter is bound to a solid impermeable backing. For example, generally a backing is of the same dimensions as the capillary flow matrix: when smaller or larger then the interface between the matrix and backing may produce a capillary path parallel to the capillary path defined by the capillary flow matrix. Suitable materials from which to form a backing include but are not limited to polyethylene, polypropylene, poly(4-methyl-butene), polystyrene, polymethacrylate, poly(ethylene terephthalate), nylon, poly(vinyl butyrate), glass, ceramics, metals, polyurethane, neoprene, latex and silicone rubber.

A material exceptionally suitable for preparing a capillary flow matrix of the present invention is glass fiber especially plastic backed glass fiber, including glass fiber derivative such as glass fiber/cellulose/polyester matrices. Glass fiber membranes are relatively thick, (typically up to 2 mm), have pore sizes of 1-40 micron and a relatively high water flow rate (when compared to typical nitrocellulose matrix) allowing large sample and reagent flow through. An additional advantage of glass fiber, as noted above, is that glass fiber is relatively thick, soft and compressible so that when pressure is applied in accordance with the teachings of the present invention, compression is local to the point of pressure.

A material exceptionally suitable for preparing a capillary flow matrix of the present invention is nitrocellulose, especially plastic backed nitrocellulose, especially having a pore size of between 0.45 and 15 micron.

A material exceptionally suitable for preparing a capillary flow matrix of the present invention is porous polyethylene, especially having a pore size of between 0.2 and 20 micron, preferably between 1 and 12 micron, available from the Porex Corporation, Fairburn Ga., USA.

The actual physical size of a capillary flow matrix of a lateral flow capillary device of the present invention is determined by many factors especially the material from which the matrix is made and the specific use or uses for which the lateral flow capillary device is intended. That said, in some embodiments a lateral flow capillary device of the present invention is a manually operated lateral flow capillary device. In embodiments of the present invention, it is generally preferred that the length of a capillary flow matrix be convenient for manual use and storage of a lateral flow capillary device, which is to say generally but not necessarily at least about 1 cm, and generally not greater than about 30 cm, not greater than about 15 cm and even not greater than about 10 cm.

In embodiments of the present invention, it is generally preferred that the width of a capillary flow matrix be sufficiently narrow to allow concentration of a material producing a signal in a small area to increase the contrast of a signal produced and reduce the liquid capacity of the capillary flow matrix, but also sufficiently wide to allow simple observation of the signal by a user, which is to say generally but not necessarily between about 1 mm and 20 mm.

In embodiments of the present invention, it is generally preferred that the capillary flow matrix be relatively thick to allow a high liquid capacity and flow rate and also ensure that the pressure applied by the rims compresses the matrix only locally. Preferably the capillary flow matrix is up to about 2 mm thick, up to about 1 mm thick, and preferably between about 0.05 and about 0.5 mm thick.

In embodiments of the present invention a capillary flow matrix is in capillary communication with a liquid drain. A liquid drain is generally a component made of a bibulous material and having a liquid absorbing capacity that is significantly larger than that of a respective capillary flow matrix. In embodiments of the present invention, a liquid drain is integrally formed with a respective capillary flow matrix. In embodiments of the present invention, a liquid drain constitutes at least one component distinct from a respective capillary flow matrix. In embodiments of the present invention, a liquid drain is of a shape or of material that allows a faster rate of capillary movement than through a respective capillary flow matrix. Suitable materials from which to fashion a drain are described, for example, in U.S. Pat. No. 4,632,901, such as, for example, fibrous materials such as cellulose acetate fibers, cellulose or cellulose derivatives, polyester, or polyolefins.

In embodiments of the present invention, reservoirs are of any suitable shape or size. As a joint between two faces may define a capillary channel, in embodiments, the inner surface of a reservoir in contact with or immediate proximity with a liquid receiving zone is continuous, for example circular, oval or otherwise curved. The volume of a given reservoir is determined by many factors and the exact implementation of a respective lateral flow capillary device. That said, a typical reservoir of a lateral flow capillary device of the present invention generally has a capacity of at least about 5 microliter, at least about 20 microliter or even at least about 50 microliter and generally no greater than about 5000 microliter, no greater than about 1000 microliter and even no greater than about 300 microliter.

Lateral Flow Capillary Device of the Present Invention

An embodiment of a lateral flow capillary device of the present invention, 24 is depicted in FIG. 2. Lateral flow capillary device 24 includes a unipath bibulous capillary flow matrix 18 having an upstream end 26 and a downstream end 28 defining a flow direction 30. Capillary flow matrix 18 of lateral flow capillary device 24 is substantially porous membrane of enforced nitrocellulose devoid of a backing layer.

Three reservoirs, a downstream reservoir 32a, a middle reservoir 32b and an upstream reservoir 32c constituting open-topped containers, are in non-capillary fluid communication (to preserve the unipath of lateral flow capillary device 24) with capillary flow matrix 18 each through a respective liquid receiving zone 34a, 34b and 34c. The distance between the edges of liquid receiving zones 34a, 34b and 34c is at least 50% of the dimension of such a liquid receiving zone in flow direction 30, although in embodiments is substantially larger. The capillary matrix between any two receiving zones is defined as an interface creation zone. Interface creation zone 35a is found between liquid receiving zones 34a and 34b. Interface creation zone 35b is found between liquid receiving zones 34b and 34c.

Each reservoir 32a, 32b or 32c contacts a respective liquid receiving zone 34a, 34b and 34c through an opening at the bottom of the reservoir constituting a hollow conduit having a rim 36a, 36b and 36c. Opposite each rim 36a, 36b and 36c are disposed supporting components 38a, 38b and 38c respectively. Rims 36a, 36b and 36c press into capillary flow matrix 18, even when capillary flow matrix is dry while supporting components 38a, 38b and 38c support capillary flow matrix 18 against the pressing so that capillary flow matrix 18 is substantially suspended between rims 36a, 36b and 36c and supporting components 38a, 38b and 38c. Rims 36a, 36b and 36c and the upper surfaces of supporting components 38a, 38b and 38c are substantially parallel to flow direction 30, ensuring that pressure applied by a rim 36a, 36b or 36c is substantially uniform about the entire surface of that rim.

As capillary flow matrix 18 is substantially compressible, the internal surface-area per unit volume of matrix 18 proximate to a rim 36a, 36b or 36c is higher than distant from a rim 36a, 36b or 36c. The presumed significance of this difference is discussed hereinbelow. The matrix material in interface creation zones 35a and 35b is unconstrained for liquid-induced swelling.

Capillary flow matrix 18 is provided with a reaction zone 20 including at least one capturing entity configured to capture a material such as an analyte or a product of a reaction involving the analyte flowing through capillary flow matrix 18 downstream from liquid receiving zones 34a, 34b and 34c.

In proximity of downstream end 28, capillary flow matrix 18 is in fluid communication with liquid drain 23.

Capillary flow matrix 18 and liquid drain 23 are substantially contained within a housing 40 such that all sides of capillary flow matrix 18 are substantially devoid of contact with housing 40. Through housing 40 above reaction zone 20 is an observation window 22 which in embodiments is simply a gap through housing 40.

For use, in accordance with the method of the present invention, a first amount of a first liquid, for example sample containing analyte is placed in downstream reservoir 32a, flows into capillary flow matrix 18 through liquid receiving zone 34a and spreads both upstream and downstream from liquid receiving zone 34a. A second amount of a second liquid, for example labeled reagent, is placed in middle reservoir 32b, flows into capillary flow matrix 18 through liquid receiving zone 34b and spreads both upstream and downstream from liquid receiving zone 34b. A third amount of a third liquid, for example signal producing component, is placed in upstream reservoir 32c, flows into capillary flow matrix 18 through liquid receiving zone 34c and spreads both upstream and downstream from liquid receiving zone 34c.

The third liquid flows upstream until all of capillary matrix 18 upstream of liquid receiving zone 34c becomes saturated with third liquid. Third liquid flows downstream from liquid receiving zone 34c until encountering second liquid flowing upstream from liquid receiving zone 34b forming a static interface 42b (see FIG. 3) somewhere in interface creation zone 35b wherethrough there is substantially no mixing of liquids. Once interface 42b is formed, and assuming that the amount of second and third liquids added is sufficient so as not to be entirely absorbed into capillary flow matrix 18, a standing column of third liquid is formed in upstream reservoir 32c as third liquid is prevented from flowing downstream by pressure applied by second liquid in middle reservoir 32b.

Second liquid flows downstream from liquid receiving zone 34b until encountering first liquid flowing upstream from liquid receiving zone 34a forming a static interface 42a somewhere in interface creation zone 35a wherethrough there is substantially no mixing of liquids. Once interface 42a is formed, and assuming that the amount of first and second liquids added is sufficient so as not to be entirely absorbed into capillary flow matrix 18, a standing column of second liquid is formed in middle reservoir 32b, the second liquid prevented from flowing downstream by pressure applied by first liquid in downstream reservoir 32a.

First liquid from downstream reservoir 32a drains down through liquid receiving zone 34a and flows downstream in flow direction 30 past reaction zone 20 on which sbp member (receptor) is immobilized. Analyte if present in the sample is captured by the sbp member while liquid is absorbed into liquid drain 23.

When all first liquid is drained from downstream reservoir 32a, the first liquid/second liquid interface begins to move downstream in flow direction 30 as second liquid from middle reservoir 32b drains down through liquid receiving zone 34b and flows downstream in flow direction 30. During this time, the second liquid/third liquid interface remains static. Labeled reagent present in the second liquid binds to complex formed at reaction zone 20, if present.

When all second liquid is drained from middle reservoir 32b, the second liquid/third liquid interface begins to move downstream in flow direction 30 as third liquid from upstream reservoir 32c drains down through liquid receiving zone 34c and flows downstream in flow direction 30. Signal producing component present in the third liquid reacts with the labeled reagent bound to complex, to generate an observable signal As discussed in the introduction, efforts have previously been made to implement methods that resemble the method of the present invention but have failed. In the prior art attempts, an interface between two liquids is formed but no standing columns of liquid is produced in a reservoir. Rather, liquids invariably leak from various locations on the capillary flow matrix, generally anywhere the capillary flow matrix makes contact with a physical object thus forming an alternate capillary pathway. For example, in a multireservoir lateral flow capillary device such as disclosed in U.S. Pat. No. 4,981,786 leakage occurs along support components on which the capillary flow matrix rests, along laterally disposed support components that hold the capillary flow in place and up the contact points of reservoirs with the capillary flow matrix, producing a flow of liquid on the top surface of the capillary flow matrix.

Thus, in contrast to the methods and lateral flow capillary devices known in the art, the teachings of the present invention allow performance of multistep reactions using a lateral flow capillary device where each step is performed with a relatively precise amount of reagent for a relatively precise duration. Since leakage is prevented and since the duration of a reaction step is accurately determined by the volume of the different liquids added, many different multistep experiments can be performed to yield repeatable results. Further, as the volume of liquid is the primary determinant of duration of a given step, the duration of a given step is easily modified if required, allowing performance of kinetic experiments.

Although, not wishing to be held to any one theory, it is believed that the reason for the failure of earlier attempts and the success of the inventor in successfully implementing the concept of liquid columns in fluid communication with a capillary flow matrix for use in performing multistep reactions is related to the forces acting on a liquid inside a capillary flow matrix and the elimination of potential alternate capillary pathways.

Water potential $\Psi$ of the liquid is the potential energy of water in a given volume (mass) and determines flow direction from a volume of a higher water potential to a volume with a lower water potential. The total water potential $\Psi$ of a volume of water is the sum of four component potentials: gravitational ($\Psi g$), matrix ($\Psi m$), osmotic ($\Psi s$), and pressure ($\Psi p$). Gravitational potential depends on the position of the water in a gravitational field. Matrix potential depends on the adsorptive forces binding water to a matrix. Osmotic potential depends on the concentration of dissolved substance in the water (e.g., a solution having a high salt concentration has a negative value). Pressure potential depends on the hydrostatic or pneumatic pressure on the water. Matrix potential is affected by both matrix and liquid properties. Matrix potential is affected by the attraction of the liquid to the matrix (hydrophilicity) and the surface area of the cavities in the matrix.

In a single reservoir lateral flow capillary device, the force acting on a liquid inside the capillary flow matrix includes the force applied by a single column of liquid in a reservoir contributing to $\Psi p$. The attraction of the liquid molecules to the internal surfaces of the capillary flow matrix ($\Psi m$) are sufficient to prevent leakage of liquid along alternate capillary paths formed, for example, where some physical object contacts the capillary flow matrix.

In a multireservoir lateral flow capillary device, described herein the force acting on a liquid inside the capillary flow matrix includes the force applied by two standing columns of liquid in two reservoirs both contributing to $\Psi p$. In such cases, $\Psi m$ that is a measure of the attraction between the liquid molecules and the internal surfaces of the capillary flow matrix are insufficient to prevent leakage of liquid along alternate capillary flow paths.

In embodiments of a lateral flow capillary device of the present invention, contact points are eliminated except at the rims of the reservoirs and, if present, at the oppositely disposed supporting components, which are pressed into the capillary flow matrix. The pressing of these components locally compresses the matrix and the pores therein, reducing the volume of the matrix proximal to these components but not changing the total internal surface area. Such pressing increases the capillary flow matrix/liquid interaction energy per unit volume in the vicinity of the components and therefore increases $\Psi m$. This increased energy is apparently sufficient to compensate for the increased force applied by the two columns of liquid. In summary, pressing of the matrix increases the binding energy in the vicinity of the contact points with the rims or supporting components, reducing the tendency to leak across the alternative capillary flow path formed at the contact point.

In embodiments of the present invention, a given interface creating zone is relatively wide relative to flanking liquid receiving zones. An advantage of such embodiments is that the size of the interface creating zone means that liquid added to one of the liquid receiving zones requires a significant period of time to travel through the interface creating zone before arriving at the neighboring liquid receiving zone. This allows addition of liquids to different reservoirs to be sequential and to be performed under more difficult (e.g., non laboratory) conditions, and even by less skilled operators. An additional advantage of a relatively wide interface creation zone is to compensate for different absorption rates of different liquids added. For example, the rate of entry of a viscous or hydrophobic liquid is relatively slow. A relatively wide interface creation zone prevents faster matrix entering liquids from travelling to a liquid receiving zone where a viscous or hydrophobic liquid is added, allowing the viscous or hydrophobic liquid to enter the matrix and create a sharp, well-defined liquid-liquid interface.

Further, it has been found that the relatively long interface creating zones leads to the formation of more sharply defined interfaces that are substantially perpendicular to the flow direction.

Many materials used as capillary flow matrices swell upon contact with water. In lateral flow capillary devices where the liquid induced swelling of the interface creation zone is constrained, for example when pressure is applied thereto from above, the swelling may be inhomogeneous and cracks may form in the matrix, locally modifying the capillary properties of the matrix. If the interface forms in a volume where the capillary properties are changed, the interface formed between liquids may be indefinite and not clear, leading to mixing of the two liquids of the interface and concomitant negative effects. In embodiments of the present invention, liquid induced swelling of the interface creation zone is unconstrained.

In embodiments of the present invention, the first liquid and second liquid are added substantially simultaneously to a respective reservoir.

In embodiments of the present invention, the first liquid and second liquid are added sequentially. When the liquids are added sequentially, the order in which the liquids is added it is of little significance, as long as a subsequent liquid is added to a respective reservoir before an earlier added liquid migrates into the liquid receiving zone of the reservoir of the subsequently added liquid.

As noted above, the method of the present invention as described above is not directed to the transport of liquids through a capillary flow matrix, but rather allows the performance of multistep reactions especially multistep specific binding assays, where each of the two liquids initiates and performs a different step of a multistep reaction, for example transport of a reagent. As is clear to one skilled in the art upon perusal of the description herein, the volume of any given liquid determines to a large degree the duration of a respective step.

Depending on the purpose for which lateral flow capillary device 24 is designed, reaction zone 20 comprises at least one capturing entity (e.g., a member of a specific binding pair) configured to capture a material (e.g., an analyte or a product of a reaction involving the analyte) flowing through the capillary flow matrix. In embodiments of the present invention, the reaction zone is in a liquid receiving zone of a respective reservoir.

In embodiments of the present invention, a lateral flow capillary device is provided with one or more reagents preloaded onto the capillary flow matrix. Such preloading of reagents is known in the art of lateral flow capillary devices, for example by drying reagents onto the matrix, for example by freeze drying, spray drying, dispensing and air drying.

In brief, a reagent is loaded onto the capillary flow matrix in such a way that a liquid added through a specific reservoir will interact with the reagent. In embodiments, at least one pre-loaded reagent is configured to react with an added analyte to produce a reaction product that is subsequently transported downstream along the capillary flow matrix. In embodiments, at least one pre-loaded reagent is configured to be solubilized by an added liquid and to be subsequently transported downstream along the capillary flow matrix. In embodiments, a preloaded reagent is located substantially in a liquid receiving zone. In embodiments, a preloaded reagent is located in the vicinity of a liquid receiving zone, specifically in an adjacent interface creation zone.

Embodiments of the present invention allow material to be preloaded both upstream and downstream of a given liquid receiving zone, allowing material to be preloaded in a relatively large region of matrix using simple methods, for example by spray-drying. Generally, material preloaded downstream from the most downstream liquid receiving zone is preloaded at any distance from the liquid receiving zone, generally (but not necessarily) between the liquid receiving zone and a reaction zone. Material preloaded in the vicinity of a most upstream liquid receiving zone is generally loaded downstream from the liquid receiving zone so that all the material will be used when liquid is introduced into the most upstream liquid receiving zone. Other preloaded material is generally preloaded either in the liquid receiving zone or somewhat upstream or somewhat downstream from the liquid receiving zone, for example up to about 30% of the length of the adjacent interface creation zone.

In embodiments of the present invention, opposite the rims of the liquid conduits of the reservoirs the matrix is attached to a substantially impermeable backing material to avoid leakage of liquids from the capillary flow matrix.

Figure 4:
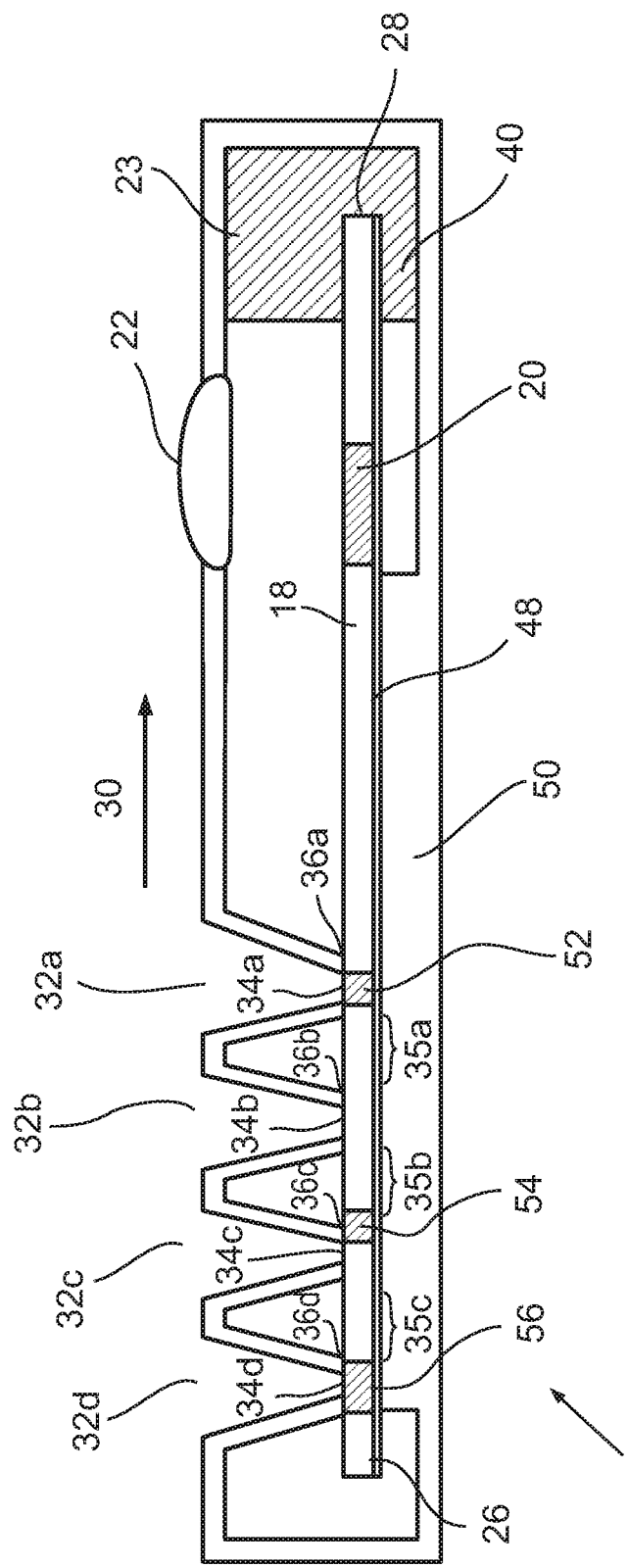
FIG. 4 schematically depicts an embodiment of a lateral flow capillary device of the present invention including four liquid reservoirs and a capillary flow matrix with a backing, in cross section.

In FIG. 4 is depicted an embodiment of a lateral flow capillary device of the present invention, 46.

In lateral flow capillary device 46, capillary flow matrix 18 is attached to a substantially impermeable backing 48. Together, capillary flow matrix 18 and impermeable backing 48 constitute a strip that rests on plateau 50, where backing 48 contacts plateau 50. Lateral flow capillary device 46 is provided with four reservoirs 32a, 32b, 32c and 32d with respective rims 36a, 36b, 36c and 36d that press the upper surface of capillary flow matrix 18. Plateau 50 is disposed opposite each rim 36 of each reservoir 32 and thus constitutes a supporting component supporting matrix 18 against the pressing of rims 36.

Lateral flow capillary device 46 is configured for the simple performance of four-step reactions.

A first reagent 52 is preloaded in liquid receiving zone 34a, first reagent 52 being a nutrient configured to cause living cells contacting first reagent 52 to express certain proteins on external membranes.

A second reagent 54 is preloaded to an area of capillary matrix 18 between liquid receiving zones 34b and 34c, second reagent 54 being a toxin.

A third reagent 56 is preloaded to liquid receiving zone 34d, third reagent 56 being an indicator that binds to the certain protein.

Reaction zone 20 includes a capture entity configured to immobilize cells.

The use of lateral flow capillary device 46 is substantially similar to the use of lateral flow capillary device 24 as described above and is clear to one skilled in the art upon perusal of the description herein.

A first liquid sample, including living cells is placed in reservoir 32a, a second liquid placed in reservoir 32b, a third liquid placed in reservoir 32c and a fourth liquid placed in reservoir 32d, sequentially or simultaneously. Three liquid interfaces are formed in the interface creation zones 35a, 35b, 35c, the interface 42a, 42b, 42c. Standing columns of liquid are produced in reservoirs 32b, 32c and 32d. When the cell-containing first liquid sample contacts first reagent in liquid receiving zone 34a, the cells begin to produce the specific metabolite. When the liquid sample reach reaction zone 20 the cells are immobilized.

When first liquid sample in reservoir 32a is exhausted, second liquid in reservoir 32b begins to flow through capillary flow matrix 18, transporting waste and other non-bound material away from reaction zone 20 towards liquid drain 23.

When second liquid in reservoir 32b is exhausted, third liquid in reservoir 32d begins to flow through capillary flow matrix 18, carrying the second reagent 54. Second reagent 54 is transported to reaction zone 20, killing immobilized cells.

When third liquid in reservoir 32c is exhausted, fourth liquid in reservoir 32d begins to flow through capillary flow matrix 18, carrying the third reagent 56. Third reagent 56 is transported to reaction zone 20, producing a visible signal on cells that expressed the certain proteins on external membranes.

Using a plurality of lateral flow capillary devices 46, substantially identical experiments are performed where only the amount of second liquid added to reservoir 32b is varied, thus varying the time between exposure of cells to first reagent 52 and killing of the cells with exposure to second reagent 54. In such a way, the kinetics of protein expression is studied.

In embodiments of the invention is used for applications other than diagnostic applications including biomolecule extraction or synthesis, for example, concentration of nucleic acids in a sample. Nucleic acid absorption particles are attached to a reaction zone of a capillary flow matrix and a sample containing nucleic acids is added under binding conditions resulting in concentration of nucleic acid from the sample. In embodiments the concentration step is followed by washing, elution and/or analysis steps.

Methods of Manufacture of a Lateral Flow Capillary Device of the Present Invention In general, manufacture and assembly of a lateral flow capillary device of the present invention is well within the ability of one skilled in the art upon perusal of the description and figures herein using any suitable method with which one skilled in the art is well acquainted. Suitable methods include methods that employ one or more techniques including but not limited to welding, casting, embossing, etching, freeform manufacture, injection-molding, microetching, micromachining, microplating, molding, spin coating, lithography or photo-lithography.

In an aspect of the present invention, a device and a kit are provided allowing the simple and cheap preparation of a custom lateral flow capillary device in accordance with the teachings of the present invention.

Figure 5A:
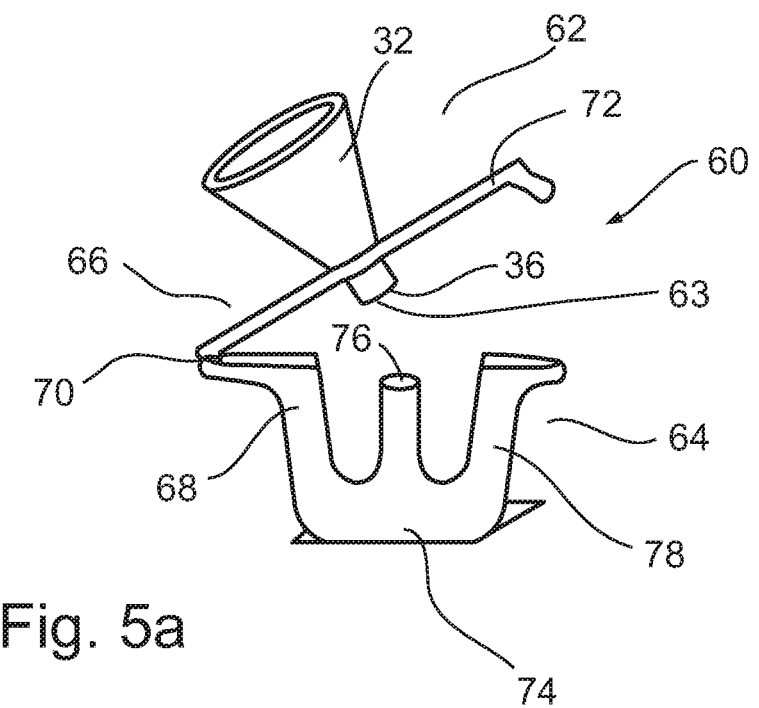
FIG. 5A schematically depicts an embodiment of a device of the present invention useful for preparing a lateral flow capillary device.

A device 60 of the present invention useful for the preparation of lateral flow capillary device is depicted in FIG. 5A. Device 60 comprises a first component 62 and a second component 64, connected through protruding extensions 66 and 68 by a hinge 70.

First component 62 includes a reservoir 32 having one wall configured to hold liquids. The lowest area of reservoir 32 is a non-capillary opening 63 defining a hollow conduit with a rim 36. In embodiments rim 36 is relatively wide, at least about 0.5 mm or even at least about 1 mm. In embodiments, rim 36 is substantially planar. To be non-capillary, in embodiments non-capillary opening 63 is relatively large, in embodiments having a cross-sectional area of at least about 1 mm$^2$, of at least about 3 mm$^2$ or even of at least about 7 mm$^2$. Opposite extension 66 and also protruding from reservoir 32 is protrusion 72.

Second component 64 includes a body 74 with a counter support platform 76 at the top end of body 74. Opposite extension 68 and also protruding from body 74 is protrusion 78.

Protrusions 72 and 78 are configured to mutually engage, interlocking (for example by "snapping together") so as to hold rim 36 and counter support platform 76 substantially parallel spaced apart at some predetermined distance.

In device 60, first component 62 is provided with two extensions 66 and 72 to engage two extensions 68 and 78 of second component 64. In embodiments, a first component and/or a second component are provided with only one extension, or with more than two such extensions each.

In device 60, extensions 66 and 68 are formed as one piece to define hinge 70. In embodiments of the present invention, extensions are configured to be reversibly or irreversibly engaged, when engaged defining a hinge. In embodiments of the present invention, extensions are configured to be reversibly or irreversibly engaged, when engaged not defining a hinge.

Figure 5B:
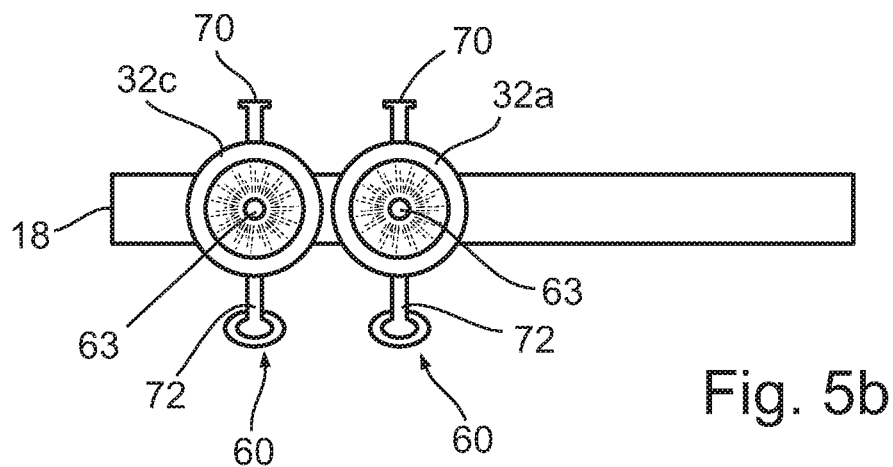
FIG. 5B schematically depicts a top view of a lateral flow capillary device made of an assembled kit of the present invention including two devices of FIG. 5A and a capillary flow matrix of plastic backed glass fiber.

The use of a device of the present invention such as device 60 in the framework of a kit of the present invention, is depicted in from the top in FIG. 5B and from the side in FIG.

Figure 5C:
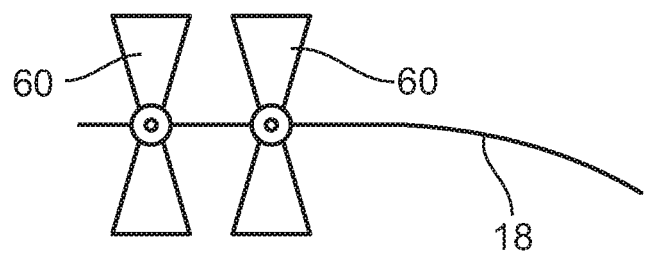
FIG. 5C schematically depicts a side view of a lateral flow capillary device made of an assembled kit of the present invention including two devices of FIG. 5A and capillary flow matrix of plastic backed glass fiber FIG. 6A schematically depicts an embodiment of a lateral flow capillary device of the present invention, exploded in cross section to show components.

5C. In FIGS. 5B and 5C, a kit of the present invention comprising two devices 60 and a strip of plastic backed glass fiber as a bibulous capillary flow matrix 18 is depicted in an assembled state, together constituting an embodiment of the device of the present invention.

For assembly, capillary flow matrix 18 of an appropriate thickness is cut to size and two devices 60 are closed over an appropriate area of capillary flow matrix 18. The thickness of capillary flow matrix 18 and the design of devices 60 is such that, when extensions 72 and 78 are mutually engaged, capillary flow matrix 18 is clamped between rim 36 and counter support platform 76 In such a state, non-capillary openings 63 defines a liquid receiving zone. Further, rim 36 presses into capillary flow matrix 18, in accordance with the teachings of the present invention.

As is clear to one skilled in the art upon perusal of the description a lateral flow capillary device, including a lateral flow capillary device of the present invention is easily custom built and modified with the use of embodiments of devices of the present invention and embodiments of kits of the present invention. For example, application of desired reagents to define a reaction zone or to preload a reagent onto a capillary matrix is simple to achieve.

In the art, for example in U.S. Pat. No. 4,981,786, is taught the introduction of sample or substrate in a downstream reservoir and addition of a carrier liquid in an upstream reservoir to transport an reagent located on a capillary flow matrix downstream to contact the sample or substrate. In an aspect of the present invention is taught a method where a sample is also used as a carrier liquid.

In the method, a lateral flow capillary device substantially as described above is used including: a first liquid receiving zone on the capillary flow matrix in fluid communication with a first reservoir, a second liquid receiving zone on the capillary flow matrix in fluid communication with a second reservoir upstream of the first reservoir, a first reagent preloaded inside the first reservoir and/or at a location on the capillary flow matrix in proximity to the first liquid receiving zone or downstream therefrom; a second reagent preloaded at a location inside the second reservoir and/or on the capillary flow matrix in proximity to the second liquid receiving zone.

A first amount of a liquid (e.g., the sample) is added to the first reservoir so that the liquid flows into the capillary flow matrix through the first liquid receiving zone to contact the first reagent, e.g., to react with the first reagent or to solubilize the first reagent.

A second amount of a liquid (either the same or different) is added to the second reservoir so that the liquid flows into the capillary flow matrix through the second liquid receiving zone to contact the second reagent. The second amount of liquid is added before, after or substantially simultaneously with the addition of the first amount of liquid.

In accordance with the teachings of the present invention, when the first amount and the second amounts are such that liquid substantially remains in the first and second reservoirs respectively, a static interface is formed between the liquid contacting the first reagent and the liquid contacting the second reagent in the interface creation zone between the two liquid receiving zones. In accordance with the teachings of the present invention as described above, the interface moves only subsequent to exhaustion of liquid from the first reservoir. In embodiments, there is a reaction zone downstream of the first liquid receiving zone on the capillary flow matrix. In embodiments, there is a reaction zone in the first liquid receiving zone. As is clear to one skilled, the advantage of this method is that an assay is made very simple.

When the liquid added to the first reservoir is the same as that added to the second reservoir, only one liquid is added (for example through a single port in communication with a number of liquid receiving zones) as in a single reservoir lateral flow capillary device but performs a multistep reaction with all the advantages thereof. This reduces the number of steps required to perform an otherwise complex multistep reaction.

EXPERIMENTAL

Reference is now made to the following examples, which together with the above descriptions, demonstrate the invention in a non limiting fashion.

Experiment 1

Figure 6A:
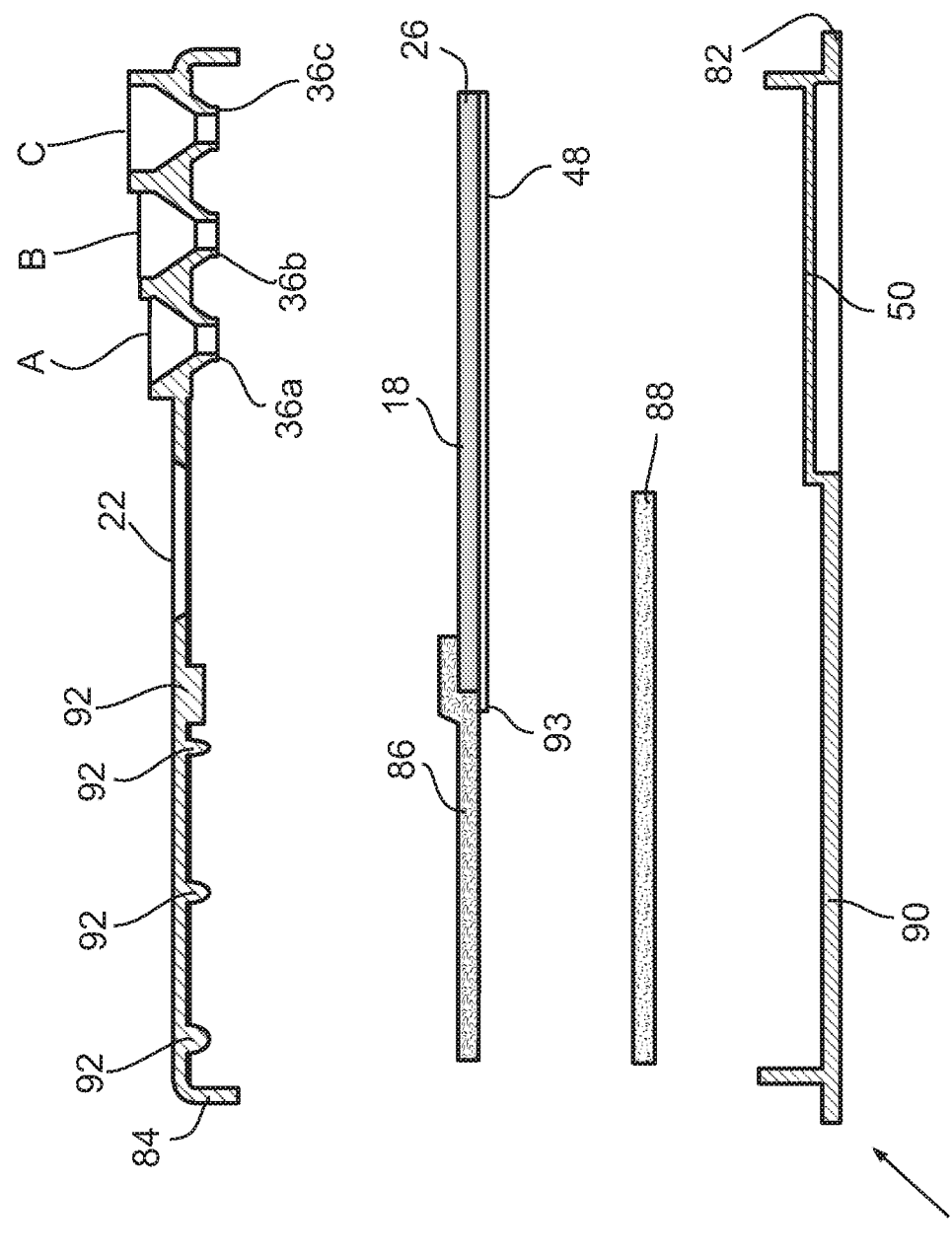
FIG. 6B schematically depicts of a capillary flow matrix of the lateral flow capillary device of FIG. 6A.
FIG. 6C is a schematic depiction of the lateral flow capillary device of FIG. 6A, assembled in cross section.

Preparation of an Embodiment of a Lateral Flow Capillary Device of the Present Invention A lateral flow capillary device such as lateral flow capillary device 80 depicted in FIGS. 6A, 6B and 6C was prepared.

A lower housing part 82 and an upper housing part 84 configured to snap together to form a closed shell holding a capillary flow matrix 18 and two liquid drains 86 and 88 were fashioned by injection molding of ABS (acrylonitrile-butadiene-styrene copolymer) plastic. Lower housing 82 was substantially a lidless box having a bottom with a plateau portion 50 and a recessed portion 90. Upper housing 84 was substantially a lid for lower housing 82 and was provided with three reservoirs A, B and C including circular rims 36a, 36b, 36c, a observation window 22, and four drain-pressing protrusions 92.

Capillary flow matrix 18, substantially a 50 mm×32 mm porous membrane of GF grade 161 glass fiber from Ahlstrom Corporation (Helsinki, Finland) attached to 55 m×32 mm×0.5 mm thick adhesive coated plastic backing (high-impact polystyrene coated with an adhesive LH-50 from Advanced Microdevices Pvt. Ltd. Ambala Cantt, India) so that the upstream end 26 of capillary flow matrix 18 was flush with an end of backing 48 and 5 mm of adhesive-coated backing protruded from upstream end 93 of backing 48.

A test line 20a and a control line 20b, constituting a reaction zone 20 were applied as two parallel lines of spots of materials to capillary flow matrix 18 using a laboratory pipette see FIG. 6B.

Test line 20a was applied as a line of spots produced by applying 1 microliter of 0.7 mg/mL Goat anti Rabbit Ab (Jackson ImmuonResearch laboratories Inc. 111-005-046) in 0.1 M phosphate buffer (pH 6.8) and 2% trehalose solution 36 mm from the upstream end of capillary flow matrix 18.

Control line 20b was applied as a line of spots produced by applying 1 microliter of Rabbit Ab 0.1 mg/ml Rabbit anti calf Alkaline Phosphates (Biogenesis 0300-1024) and 0.4 mg/ml Rabbit IgG I 5006 (Sigma-Aldrich, St. Louis, Mo., USA) in 0.1 M phosphate buffer (pH 6.8) and 2% trehalose solution 42 mm from the upstream end of capillary flow matrix 18.

After application of the spots, capillary flow matrix 18 was dried at 37° C. for 15 minutes, treated with a solution of 0.5% gelatin, 2.5% Bacto-Tryptone, 1% trehalose in PBS and then dried at 37° C. for an additional 2 hours.

Two liquid drains 86 and 88 were prepared of highly absorbent pure cellulose paper with a very high flow rate (190 mm/30 min) Chr. 17 (Whatman). Upper liquid drain 86 was 32 mm×36 mm and attached to the adhesive of protruding upstream end 93 of backing 48 abutting capillary flow matrix 18 so as to ensure fluid communication therewith. Lower liquid drain 88 was 7.8 mm×83 mm.

As depicted in FIG. 6C, for assembly of lateral flow capillary device 80, lower liquid drain 88 was laid in recess 90 of lower housing 82, capillary flow matrix 18 together with upper liquid drain 86 were placed on plateau 50 of lower housing 82 with backing 48 making contact with plateau 50. Upper housing 84 was pressed into place to engage and snap together with lower housing 82 so that rims 36 of reservoirs A, B and C pressed into capillary flow matrix 18 to define liquid receiving zones 34a, 34b and 34c and so that drain pressing protrusions 92 pressed the end of upper liquid drain 86 to contact lower liquid drain 88.

Experiment 2

Use of a Lateral Flow Capillary Device to Study Enzymatic Reaction

Three lyophilized reagents were prepared:
Reagent A
  11-dehydro-TxB2-antiserum reagent—150 ul Rabbit anti 11-dehydro-TXB, 2999-044 (Assay Designs, Inc.) diluted 1:15000 in 1% BSA, 0.25% TWEEN-20, 0.1 mM $ZnCl_2$, 1 mM $MgCl_2$ in PBS buffer pH 7.4 was placed in a vial, cooled to −80° C. and lyophilized for 24 hours.
Reagent B
  Enzyme labeled 11-dehydro-TxB2 conjugate—150 ul 11-dehydro-TxB2-Alkaline Phosphatase conjugate, 1:80 DCC (Assay Designs, Inc.) diluted 1:30,000 in 1% BSA, 0.25% TWEEN-20, 0.1 mM $ZnCl_2$, 1 mM $MgCl_2$ in PBS buffer pH 7.4 was placed in a vial, cooled to −80° C. and lyophilized for 24 hours.
Reagent C
  AP substrate—BCIP/NBT prepared according to manufacturer instruction: stock preparation—1 tablet BCIP, B0274 (Sigma-Aldrich, St. Louis, Mo. USA) dissolved in 1 ml DMF, 1 tablet NBT, N55141 (Sigma-Aldrich, St. Louis, Mo., USA) dissolved in 1 ml water. 300 ul of the combined solution, 33 ul BCIP, 333 ul NBT stock solutions, in 10 ml 0.1M Tris buffer pH 9.7, were placed in a vial, cooled to −80° C. and lyophilized for 24 hours.

Three lateral flow capillary devices were prepared:
A first lateral flow capillary device was prepared substantially as described above with dry PBS buffer placed in reservoir A, reagent B placed in reservoir B and reagent C placed in reservoir C.

A second lateral flow capillary device was prepared substantially as described above with reagent A placed in reservoir A, dry PBS solution placed in reservoir B and reagent C placed in reservoir C.

A third lateral flow capillary device was prepared substantially as described above with reagent A placed in reservoir A, reagent B placed in reservoir B and reagent C placed in reservoir C.

To each of the three lateral flow capillary devices was added double distilled water: 150 microliter in reservoir A, 150 microliter in reservoir B and 300 microliter in reservoir C, one reservoir after the other. A standing column of liquid was seen in each reservoir and, as described above in accordance with the teachings of the present invention, the liquid drained first from reservoir A, then from reservoir B and finally from reservoir C. When all liquid drained away from reservoir C, the enzymatic reaction was stopped by the addition of a 120 ul 0.25M sulfuric acid stop solution to reservoir C.

The colors of the test lines and control lines were measured using a PART Pro Reader (LRE Technology Partner GmbH) and depicted in FIG. 7.

As seen in FIG. 7, in the first lateral flow capillary device, no color was observed at the test line and color was observed at the control line; in the second lateral flow capillary device, color was observed at neither the test line nor at the control line; and in the third lateral flow capillary device, color was observed at both the test line and at the control line.

The results indicate that the lateral flow capillary devices operated as expected.

Experiment 3

Txb2 Detection for Comparing a Multireservoir Lateral Flow Capillary Device with a Single Reservoir Lateral Flow Capillary Device for Performing a Multistep Reaction Two lateral flow capillary devices A and B were prepared substantially as described above in Experiment 1 with a 50 mm×32 mm capillary flow matrix and two capillary flow reactors C and D were prepared with a shorter 40 mm×32 mm capillary flow matrix and assembled so that only rim 34a of reservoir a was in contact with capillary flow matrix 18.

Five reaction liquids were prepared:
  1. A diluent solution of 1% BSA, 0.25% TWEEN-20, 0.1 mM $ZnCl_2$, 1 mM $MgCl_2$ in PBS buffer pH 7.4;
  2. Reagent A of Rabbit anti 11-dehydro-TXB2 (Assay Designs, Inc. 999-044) diluted 1:15,000 in 1% BSA, 0.25% TWEEN-20, 0.1 mM $ZnCl_2$, 1 mM $MgCl_2$ in PBS buffer pH 7.4;
  3. Reagent B of 11-dehydro-TxB2-Alkaline Phosphatase conjugate (Assay Designs, Inc. 1:80 DCC) diluted 1:30,000 in 1% BSA, 0.25% TWEEN-20, 0.1 mM $ZnCl_2$, 1 mM $MgCl_2$ in PBS buffer pH 7.4;
  4. Reagent C of BCIP/NBT prepared according to manufacturer instruction: stock preparation—1 tablet BCIP (Sigma-Aldrich B0274) dissolving in 1 ml DMF, 1 tablet NBT (Sigma-Aldrich N55141) dissolving in 1 ml water, final solution: 33 ul BCIP, 333 ul NBT stock solutions, in 10 ml 0.1M Tris buffer pH 9.7; and
  5. Reagent D, a stop solution of 0.25M sulfuric acid.

Use of Multireservoir Lateral Flow Capillary Devices
150 ul of reagent A, 150 ul of reagent B and 300 ul of reagent C were simultaneously added to reservoirs A, B, and C respectively of lateral flow capillary device A.

150 ul of diluent solution, 150 ul of reagent B and 300 ul of reagent C were simultaneously added to reservoirs A, B, and C respectively of lateral flow capillary device B.

After complete sequential draining of all three solutions in the order A, B and C, 120 ul reagent D was added to reservoir C.

Figure 8A:
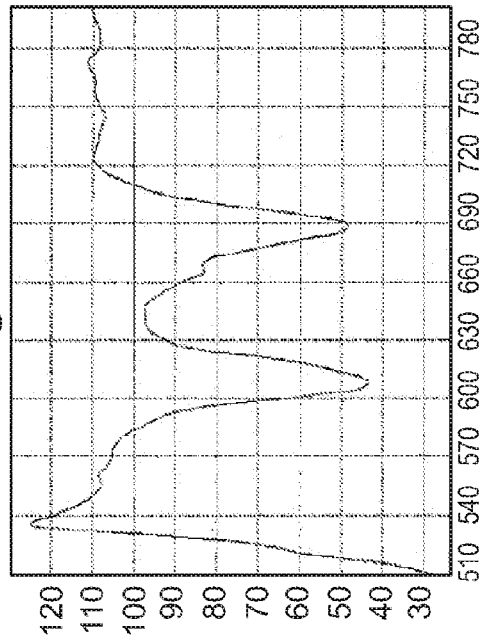
FIG. 8 are results of experiment 3 described below, comparing detection of an analyte in accordance with the teachings of the present invention (8A and 8B) and using a single reservoir lateral flow capillary device (8C and 8D)
Figure 8C:
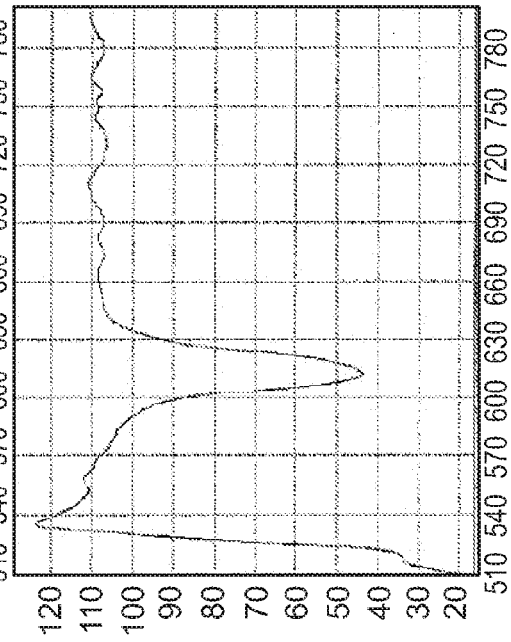
Figure 8B:
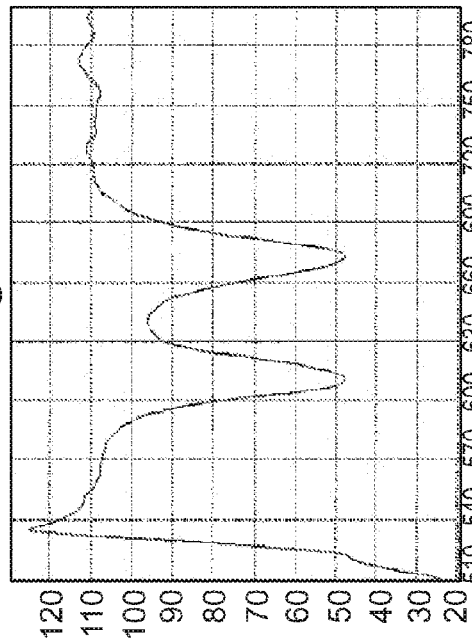

The colors of the test lines and control lines were measured using a PART Pro Reader (LRE Technology Partner GmbH) and depicted in FIGS. 8A and 8B.

Use of Single Reservoir Lateral Flow Capillary Devices
To reservoir A of lateral flow capillary device C were added one after the other 150 ul of reagent A, 150 ul of reagent B, 300 ul of reagent C and 120 ul of reagent D, each succeeding liquid only after the previous liquid had completely drained away from the reservoir.

To reservoir A of lateral flow capillary device D were added one after the other 150 ul of diluent solution, 150 ul of reagent B and 300 ul of reagent C and 120 ul of reagent D, each succeeding liquid only after the previous liquid had completely drained away from the reservoir.

Figure 8D:
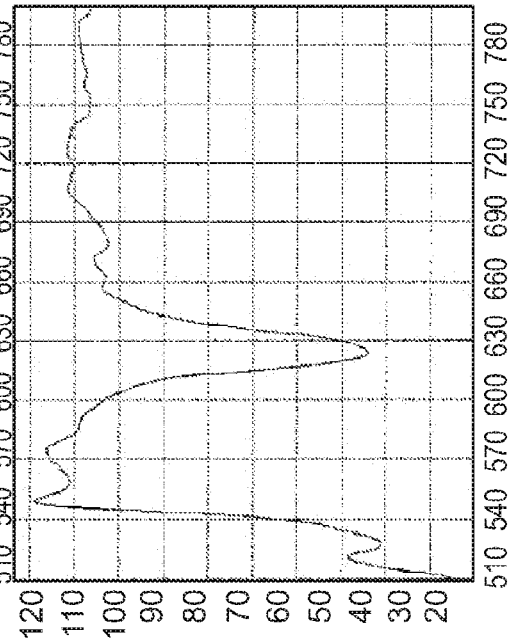

The colors of the test lines and control lines were measured using a PART Pro Reader (LRE Technology Partner GmbH) and depicted in FIGS. 8C and 8D.

From comparing FIGS. 8A and 8C and FIGS. 8B and 8D it is seen that the results obtained using a multireservoir lateral flow capillary flow device when adding all reagents at the beginning of the experiment are substantially the same as the results obtained using a single reservoir lateral capillary flow device when adding the reagents during the experiment.

The time duration of each reservoir draining was measured and the flow rat was calculated (minutes for 100 ul liquid to travel 1 cm through the capillary flow matrix results shown in Table 1:

TABLE 1

| Flow [minutes for 100 ul to travel 1 cm] | | | | | |
|---|---|---|---|---|---|
| Liquid | Reservoir | device A | device B | device C | device D |
| A | A | 0:00:57 | 0:00:57 | | |
| B | B | 0:01:10 | 0:01:16 | | |
| C | C | 0:01:08 | 0:01:10 | | |
| D | C | 0:01:16 | 0:01:19 | | |
| A | A | | | 0:00:55 | 0:00:54 |
| B | A | | | 0:01:14 | 0:01:10 |
| C | A | | | 0:01:12 | 0:01:08 |
| D | A | | | 0:01:16 | 0:01:10 |

Experiment 4

Calibration Curve for
11-dehydro-TxB2-Competition Assay

Five lateral flow capillary devices substantially as described above in experiment 1

Five reagent liquids were prepared:

1. A diluent solution of 1% BSA, 0.25% TWEEN-20, 0.1 mM $ZnCl_2$, 1 mM $MgCl_2$ in PBS buffer pH 7.4;

2. Reagent A of Rabbit anti 11-dehydro-TXB2 (Assay Designs, Inc. 999-044) diluted 1:1,500 in 1% BSA, 0.25% TWEEN-20, 0.1 mM $ZnCl_2$, 1 mM $MgCl_2$ in PBS buffer pH 7.4;

3. Reagent B of 11-dehydro-TxB2-Alkaline Phosphatase conjugate (Assay Designs, Inc. 1:80 DCC) diluted 1:3,000 in 1% BSA, 0.25% TWEEN-20, 0.1 mM $ZnCl_2$, 1 mM $MgCl_2$ in PBS buffer pH 7.4;

4. Reagent C of BCIP/NBT was prepared according to manufacturer instruction: stock preparation—1 tablet BCIP (Sigma-Aldrich B0274) dissolving in 1 ml DMF, 1 tablet NBT (Sigma-Aldrich N55141) dissolving in 1 ml water. Final solution: 33 ul BCIP, 333 ul NBT stock solutions, in 10 ml 0.1M Tris buffer pH 9.7; and 5. Reagent D, a stop solution of 0.25M sulfuric acid.

Five sample solutions were prepared containing 5, 1, 0.2, 0.04, 0 ng/ml of 11-dehydro-TxB2 (80-0735) analyte from Assay Designs, Inc dissolved in 1% BSA, 0.25% TWEEN-20, 0.1 mM $ZnCl_2$, 1 mM $MgCl_2$ in PBS buffer solution pH 7.4.

To the first lateral flow capillary device, 150 ul of a mixture of 15 ul reagent A and 135 ul sample containing 5 ng/ml analyte, 150 ul of a mixture of 15 ul reagent B and 135 ul sample containing 5 ng/ml analyte and 300 ul of reagent C were added to reservoirs A, B, and C respectively.

To the second lateral flow capillary device, 150 ul of a mixture of 15 ul reagent A and 135 ul sample containing 1 ng/ml analyte, 150 ul of a mixture of 15 ul reagent B and 135 ul sample containing 1 ng/ml analyte and 300 ul of reagent C were added to reservoirs A, B, and C.

To the third lateral flow capillary device, 150 ul of a mixture of 15 ul reagent A and 135 ul sample containing 0.2 ng/ml analyte, 150 ul of a mixture of 15 ul reagent B and 135 ul sample containing 0.2 ng/ml analyte and 300 ul of reagent C were added to reservoirs A, B, and C.

To the fourth lateral flow capillary device, 150 ul of a mixture of 15 ul reagent A and 135 ul sample containing 0.04 ng/ml analyte, 150 ul of a mixture of 15 ul reagent B and 135 ul sample containing 0.04 ng/ml analyte and 300 ul of reagent C were added to reservoirs A, B, and C respectively.

To the fifth lateral flow capillary device, 150 ul of a mixture of 15 ul reagent A and 135 ul sample containing 0 ng/ml analyte, 150 ul of a mixture of 15 ul reagent B and 135 ul sample containing 0 ng/ml analyte and 300 ul of reagent C were added to reservoirs A, B, and C respectively.

After complete draining of all three reservoirs in the order A, B and C in accordance with the teachings of the present invention, 120 ul reagent D was added to reservoir C of each of the lateral flow capillary device.

The colors of the test lines and control lines were measured using a PART Pro Reader (LRE Technology Partner GmbH) and the bound level of the labeled analyte at each analyte concentration was calculated as the ratio b/b0 between the reflection at each concentration 5, 1, 0.2, 0.04 ng/ml (b) and the reflection at 0 ng/ml (b0). A calibration curve was made by plotting the results, FIG. 9.

Experiment 5

Quantitative Determination of 11-dehydro-TxB2 in Urine

Three lateral flow capillary devices substantially similar to the third lateral flow capillary device described in Experiment 2 were prepared with lyophilized reagent A in reservoir A, lyophilized reagent B in reservoir B and lyophilized reagent C in reservoir C.

To each of the three lateral flow capillary devices was added: 150 ul urine sample to reservoir A, 150 ul of the same urine sample to reservoir B and 300 ul double distilled water to reservoir C. After complete sequential draining of reservoirs A, B, and C in accordance with the teachings of the present invention, 120 ul stop solution D was added to reservoir C.

Figure 9:
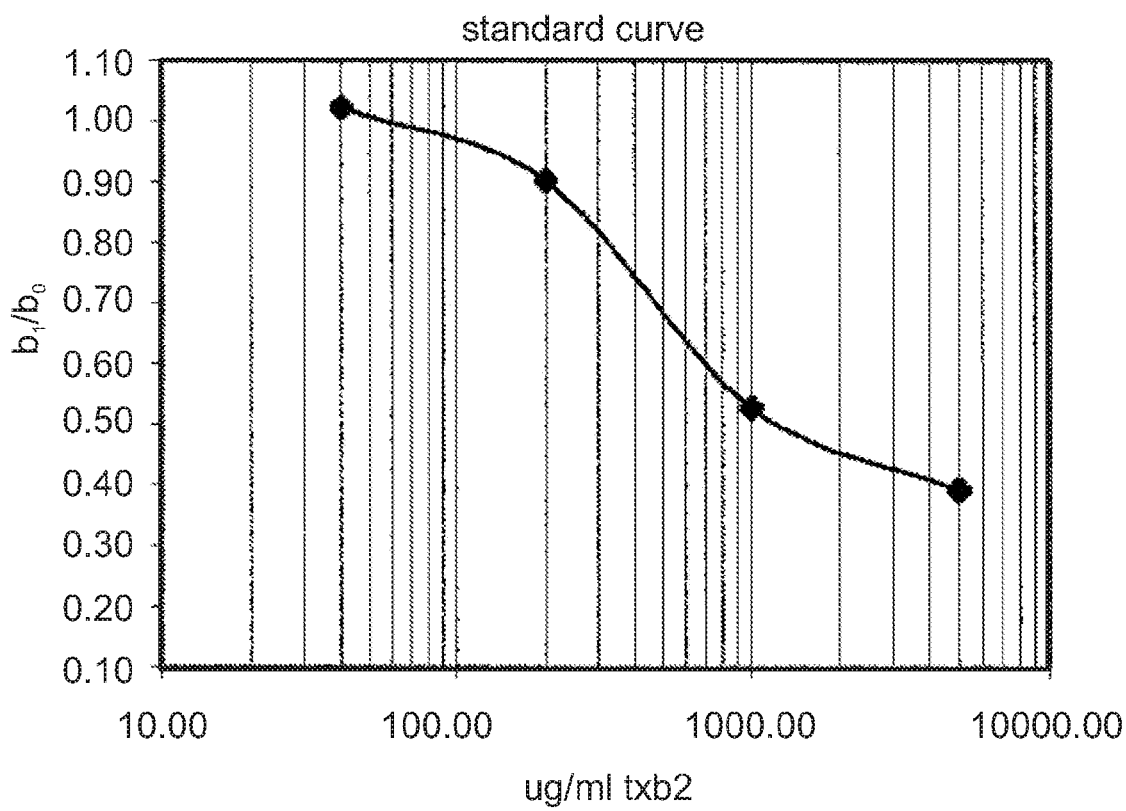
FIG. 9 are results of experiment 4 described below, a calibration curve for 11-dehydro-TxB2-competition assay acquired in accordance with the teachings of the present invention.

The colors of the test lines and control lines were measured using a PART Pro Reader (LRE Technology Partner GmbH) and the concentration of 11-dehydro-TxB2 analyte in each urine sample determined with reference to the calibration curve of FIG. 9. The first urine sample was determined to contain 5251 pg/mL, the second urine sample 907 pg/ml and the third urine sample 540 pg/ml 11-dehydro-TxB2.

Experiment 6

Sequential Liquid Flow in a Lateral Flow Capillary Device

A lateral flow capillary device E was prepared substantially as described above in Experiment 1 with a 50 mm×32 mm capillary flow matrix. A lateral flow capillary device F were prepared with a shorter 40 mm×32 mm capillary flow matrix and assembled so that only rim 36a of reservoir A was in contact with capillary flow matrix 18. The capillary flow matrices of both lateral flow capillary devices E and F were devoid of reaction zones and only treated with a solution of 0.5% gelatin, 2.5% Bacto-Tryptone, 1% trehalose in PBS.

A number of reaction liquids, diluent solution, reagent A (yellow), reagent B (blue) and reagent C (red) were prepared as described in Experiment 3

Use of Multireservoir Lateral Flow Capillary Device 150 ul of reagent A, 150 ul of reagent B and 300 ul of reagent C were added, one after the other, to reservoirs A, B, and C respectively of lateral flow capillary device E. Sequential draining of reservoirs A, B, and C in accordance with the teachings of the present invention was observed with a sharp interface that was observed to move in accordance with the teachings of the present invention.

Use of Single Reservoir Lateral Flow Capillary Device

To reservoir A of lateral flow capillary device F were added one after the other 150 ul of reagent A, 150 ul of reagent B and 300 ul of reagent C each succeeding liquid only after the previous liquid had completely drained away.

The draining time for each reservoir was measured and listed in Table 2:

TABLE 2

| Liquid | Reservoir | Draining time device E | device F |
|---|---|---|---|
| A | A | 0:3:07 | |
| B | B | 0:10:01 | |
| C | C | 0:25:20 | |
| A | A | | 0:03:03 |
| B | A | | 0:08:14 |
| C | A | | 0:18:13 |

Experiment 7

Detection of HIV 1 Antibodies in Blood Serum Sample

A lateral flow capillary device was prepared substantially as described above in Experiment 1 with a control line 20b as described in Experiment 1 but with a test line 20a applied as a line of spots produced by applying 1 microliter of 0.7 mg/mL HIV 1 recombinant protein antigen HIV-101 (ProSpec-Tany TechnoGene LTD) in 0.1 M phosphate buffer (pH 6.8) and 2% trehalose solution 36 mm from the upstream end of capillary flow matrix 18.

In reservoir A was placed a lyophilized (as described above) solution of 1 mg/ml biotinylated synthetic gp41 and gp120 peptides diluted in 1% BSA, 1% fetal bovine serum, 0.5% TWEEN-20 in PBS buffer pH 7.4.

In reservoir B was placed a lyophilized (as described above) solution of Streptavidin-Alkaline Phosphatase conjugate (Jackson ImmuonResearch laboratories Inc. 003-050-083) diluted in 1% BSA, 0.5% TWEEN-20, 0.1 mM $ZnCl_2$, 1 mM $MgCl_2$ in PBS buffer pH 7.4.

In reservoir C was placed a lyophilized (as described above) solution of BCIP/NBT prepared according to the manufacturer instructions stock preparation—1 tablet BCIP (Sigma-Aldrich B0274) dissolving in 1 ml DMF, 1 tablet NBT (Sigma-Aldrich N55141) dissolving in 1 ml water. A final solution: 33 ul BCIP, 333 ul NBT stock solutions, in 10 ml 0.1M Tris buffer pH 9.7.

150 ul of a serum sample, 150 ul of a serum sample and 300 ul of double distilled water were added, one after the other, to reservoirs A, B, and C respectively of the lateral flow capillary device. Sequential draining of reservoirs A, B, and C in accordance with the teachings of the present invention was observed. After the liquid in reservoir C completely drained away 120 ul reagent D (0.25 M sulfuric acid stop solution) was added to reservoir C.

The appearance of two colored dotted lines, one at the test line and the other at the control line, indicated the presence of antibodies for HIV 1 in the serum sample.

Experiment 8

Detection of Hepatitis B Surface Antigen in Blood Serum Sample Using a Two Reservoir Lateral Flow Capillary Device A lateral flow capillary device was prepared substantially as described above in Experiment 1 excepting that the capillary flow matrix was 45 mm×32 mm and the lower liquid drain was 7.8 mm×73 mm and with a control line 20b as described in Experiment 1 but with a test line 20a applied as a line of spots produced by applying 1 microliter of 0.7 mg/mL mouse monoclonal anti-HBsAg antibody (Fitzgerald Industries International, Inc. 10-H05) in 0.1 M phosphate buffer (pH 6.8) and 2% trehalose solution. When assembled in the housing, the rims 34a and 34b of reservoirs A and B were in contact with capillary flow matrix 18 but the rim 36c of reservoir C was not in contact with the capillary flow matrix 18.

In reservoir A was placed a lyophilized (as described above) solution of rabbit anti-HBsAg Alkaline Phosphatase conjugate diluted in 1% BSA, 1% fetal bovine serum, 0.5% TWEEN-20, 0.1 mM $ZnCl_2$, 1 mM $MgCl_2$ in PBS buffer pH 7.4.

In reservoir B was placed a lyophilized (as described above) solution of BCIP/NBT prepared according to the manufacturer instructions stock preparation—1 tablet BCIP (Sigma-Aldrich B0274) dissolving in 1 ml DMF, 1 tablet NBT (Sigma-Aldrich N55141) dissolving in 1 ml water. A final solution: 33 ul BCIP, 333 ul NBT stock solutions, in 10 ml 0.1M Tris buffer pH 9.7.

300 ul of a serum sample and 300 ul of double distilled water were added, one after the other, to reservoirs A and B respectively of the lateral flow capillary device. Sequential draining of reservoirs A and B in accordance with the teachings of the present invention was observed. After the liquid in reservoir B completely drained away 120 ul 0.25 M sulfuric acid stop solution was added to reservoir B.

The appearance of two colored dotted lines, one at the test line and the other at the control line, indicated the presence of Hepatitis B Surface Antigen in the serum sample.

Experiment 9

Detection of Fluorescent Signal-High Volume Samples

Four lateral flow capillary devices were prepared substantially as described in Experiment 1 where reaction zone 20 included only a test line 20a but no control line.

A reagent H was prepared of Rabbit anti mouse-cy5 antibody (Jackson ImmuonResearch laboratories Inc. 515-175-045) diluted in 1% BSA, 1% fetal bovine serum, 0.5% TWEEN-20, 0.1 mM $ZnCl_2$, 1 mM $MgCl_2$ in PBS buffer pH 7.4.

200 ul of reagent H were added to reservoir C of the first lateral flow capillary device.

200 ul of reagent H were added to reservoirs B and C of the second lateral flow capillary device.

200 ul of reagent H were added to reservoirs A, B and C of the third lateral flow capillary device.

200 ul of reagent H were added to reservoirs A, B and C of the fourth lateral flow capillary device. After complete draining of liquid from reservoir C, and additional 200 ul of reagent H were added to reservoir C.

Figure 10:
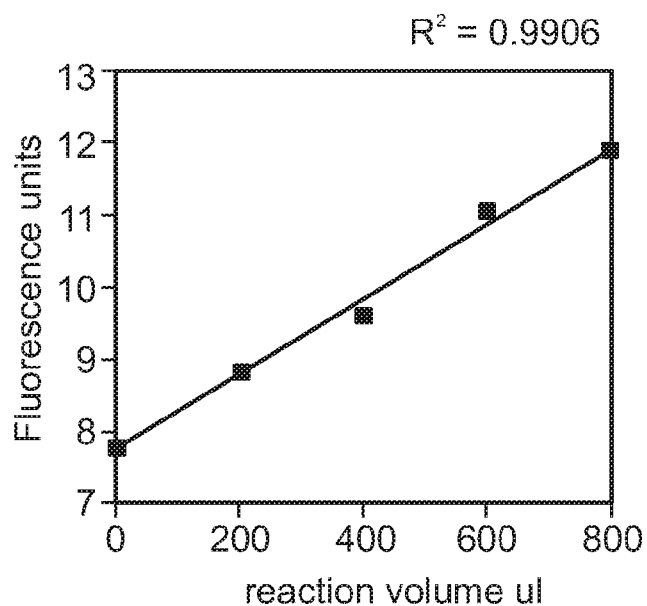
FIG. 10 are results of experiment 10 described below, showing the correlation between the intensity of florescence emitted by a reaction zone of a lateral flow capillary device of the present invention and the total volume of liquid added.

There was a linear correlation between the intensity of fluorescence emitted by a given test line 20b as measured by PART Immuno Reader (LRE Technology Partner GmbH) and the total volume of liquid added to the respective lateral flow capillary device, see the graph in FIG. 10.

Experiment 10

Detection of HPV 16 DNA Sequence

A lateral flow capillary device were prepared substantially as described in Experiment 1 where capillary flow matrix 18 was nitrocellulose Prima 40 (Schleicher & Schuell).

A reaction zone 20 was prepared by applying a line of spots 36 mm from the upstream end of the capillary flow matrix, each spot produced by applying 1 microliter of 5 ug/mL oligonucleotide probe (5'GTTTCAGGACCCACAGGAGC-GACCC (nt 106-130)) (SEQ ID NO:1) in 1.5 M NaCl and 0.15M Na-citrate, pH 7.0 solution. After drying at 37° C. for 15 minutes, capillary flow matrix 18 was irradiated with ultraviolet light for 5 minutes to fix the DNA to capillary flow matrix 18.

Cellular DNA from CaSki cells was subjected to 30 PCR amplification cycles using a first primer (5'AAGGGCG-TAACCGAAATCGGT (nt 26-46)) (SEQ ID NO:2) and a biotinylated second primer (5'GTTGTTTGCAGCTCT-GTGC (nt 150-168)) (SEQ ID NO:3) specific for HPV 16 sequences. PCR was ended with a denaturation step and fast chilling to 4° C.

In reservoir A of the lateral flow capillary device was placed 50 ul of denatured biotinylated PCR product, diluted 1:10 in ice chilled 0.6 M NaCl, 0.02% Ficoll 400, 0.02% gelatin, 1% PVP, 20 mM phosphate buffer pH 7.5 solution.

In reservoir B of the lateral flow capillary device was placed 50 ul of Streptavidin-Alkaline Phosphatase conjugate (Jackson ImmuonResearch laboratories Inc. 003-050-083) diluted in 1% BSA, 0.5% TWEEN 20, 0.1 mM $ZnCl_2$, 1 mM $MgCl_2$ in PBS buffer pH 7.4.

In reservoir C of the lateral flow capillary device was placed 150 ul of reagent C, BCIP/NBT was prepared according to manufacturer instruction: stock preparation—1 tablet BCIP (Sigma-Aldrich B0274) dissolving in 1 ml DMF, 1 tablet NBT (Sigma-Aldrich N55141) dissolving in 1 ml water. Final solution: 33 ul BCIP, 333 ul NBT stock solutions, in 10 ml 0.1M Tris buffer pH 9.7.

Sequential draining of reservoirs A, B, and C in accordance with the teachings of the present invention was observed. After the liquid in reservoir C completely drained away, a purple colored line at the reaction zone indicated the presence of the HPV 16 DNA sequences.

Experiment 11

Detection of HIV-1 Antibodies Using Lyophilized Conjugate in a Reaction Zone.

A lateral flow capillary device was prepared substantially as described above in Experiment 7 except that lyophilized reagents were placed as follows:

In the reaction zone was placed lyophilized (as described above) solution of 1 mg/ml biotinylated synthetic gp41 and gp120 peptides diluted in 1% BSA, 1% fetal bovine serum, 0.5% TWEEN-20 in PBS buffer pH 7.4

Reservoir A was kept empty.

In reservoir B was placed a lyophilized (as described above) solution of Streptavidin-Alkaline Phosphatase conjugate (Jackson ImmuonResearch laboratories Inc. 003-050-083) diluted in 1% BSA, 0.5% TWEEN-20, 0.1 mM $ZnCl_2$, 1 mM $MgCl_2$ in PBS buffer pH 7.4.

In reservoir C was placed a lyophilized (as described above) solution of BCIP/NBT prepared according to the manufacturer instructions stock preparation—1 tablet BCIP (Sigma-Aldrich B0274) dissolving in 1 ml DMF, 1 tablet NBT (Sigma-Aldrich N55141) dissolving in 1 ml water. A final solution: 33 ul BCIP, 333 ul NBT stock solutions, in 10 ml 0.1M Tris buffer pH 9.7.

150 ul of a serum sample were applied to capillary flow matrix 18 through observation window 22, 150 ul of serum sample were added to reservoir B and 300 ul of double distilled water were added to reservoir C. Sequential draining of reservoirs B and C in accordance with the teachings of the present invention was observed. After the liquid in reservoir C completely drained away 120 ul 0.25 M sulfuric acid stop solution was added to reservoir C.

The appearance of two colored dotted lines, one at the test line and the other at the control line, indicated the presence of antibodies for HIV 1 in the serum sample.

In the experimental section above the teachings of the present invention were exemplified for the study of enzymatic reactions and for the detection of specific analytes in a sample. As is clear to one skilled in the art upon perusal of the description herein, the teachings of the present invention are applicable to many different fields where the performance of multistep reactions are required, including but not limited to environmental chemistry, cell biology and biochemistry.

Methods and processes have been described herein as a series of steps in an order selected as being the easiest to understand. It must be emphasized that such order is not limiting, and any method or process described herein may be implemented where the steps are performed in any reasonable order to achieve the desired result.

Although the invention has been described in conjunction with specific embodiments thereof, it is evident that many alternatives, modifications and variations will be apparent to those skilled in the art. Accordingly, the present invention is intended to embrace all such alternatives, modifications and variations that fall within the spirit and broad scope of the appended claims. For example, the teachings of the present invention have been described where a reaction takes place at room temperature. In embodiments of the present invention, a lateral flow capillary device is maintained in warmer or colder environment, for example a freezer, a refrigerator, or an incubator so that a reaction is performed at a temperature that is hotter or colder than room temperature or to ensure that a specific desired temperature is maintained. Embodiments in which a lateral flow capillary device is maintained at a controlled temperature include during an entire reaction or during only part of a reaction.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

All publications, patents and patent applications mentioned in this specification are herein incorporated in their entirety by reference into the specification, to the same extent as if each individual publication, patent or patent application was specifically and individually indicated to be incorporated herein by reference. In case of conflict, the specification herein, including definitions, will control. Citation or identification of any reference in this application shall not be construed as an admission that such reference is available as prior art to the present invention.

What is claimed is:

1. A lateral flow capillary system, comprising:
   a) a unipath bibulous capillary flow matrix having a thickness; and
   b) at least two devices useful for preparation of said lateral flow capillary system engaged about said matrix, each of said devices comprising:
   a first component comprising a single reservoir with at least one wall configured to hold liquids and a lowest area, said lowest area comprising a non-capillary opening comprising a hollow conduit with a rim and at least one extension protruding from an outer surface of said wall; and
   a second component comprising a body with a counter-support platform at a top-end and at least one extension protruding from said body
   wherein a said extension of said first component and a said extension of said second component are configured to mutually engage so that said rim and said counter-support platform are spaced apart by a distance and substantially parallel, wherein said distance is sufficient so that a said rim contacts said matrix when said first component and said second component are engaged about said matrix.

2. The system of claim 1, wherein the bibulous capillary flow matrix is attached to a substantially impermeable backing material.

3. The system of claim 2, wherein said backing material comprises polyethylene, polypropylene, poly(4-methylbutene), polystyrene, polymethylacrylate, poly(ethylene terephthalate), nylon, poly(vinyl butyrate), glass, ceramic, metal, polyurethane, latex, or silicone rubber.

4. The system of claim 1, wherein the at least two devices useful for preparation of said lateral flow capillary device are adjacent.

* * * * *

SEQUENCE LISTING

<160> NUMBER OF SEQ ID NOS: 3

<210> SEQ ID NO 1
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 1
gtttcaggac ccacaggagc gaccc         25

<210> SEQ ID NO 2
<211> LENGTH: 21
<212> TYPE: DNA
<213> ORGANISM: Artificial Sequence
<220> FEATURE:
<223> OTHER INFORMATION: Synthetic primer

<400> SEQUENCE: 2
aagggcgtaa ccgaaatcgg t         21

<210> SEQ ID NO 3
<211> LENGTH: 19
<212> TYPE: DNA
<213> ORGANISM: Artificial Sequence
<220> FEATURE:
<223> OTHER INFORMATION: Synthetic primer

<400> SEQUENCE: 3
gttgtttgca gctctgtgc         19